(12) United States Patent
Prevost et al.

(10) Patent No.: US 8,710,091 B2
(45) Date of Patent: Apr. 29, 2014

(54) IMIDAZOLIDINE-2,4-DIONE DERIVATIVES, AND USE THEREOF AS A CANCER DRUG

(75) Inventors: Grégorie Prevost, Antony (FR); Serge Auvin, Palaiseau (FR); Christophe Lanco, Dourban (FR); Anne-Marie Liberatore, Auffargis (FR); Olivier Lavergne, Palaiseau (FR)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 0 days.

(21) Appl. No.: 13/264,971

(22) PCT Filed: Apr. 16, 2010

(86) PCT No.: PCT/FR2010/000315
§ 371 (c)(1),
(2), (4) Date: Dec. 16, 2011

(87) PCT Pub. No.: WO2010/119193
PCT Pub. Date: Oct. 21, 2010

(65) Prior Publication Data
US 2012/0083514 A1 Apr. 5, 2012

(30) Foreign Application Priority Data

Apr. 17, 2009 (FR) ...................... 09 01865

(51) Int. Cl.
*A61K 31/4166* (2006.01)
*C07D 233/40* (2006.01)
(52) U.S. Cl.
USPC ...................... 514/389; 548/316.7
(58) Field of Classification Search
USPC ...................... 548/316.7; 514/389
See application file for complete search history.

(56) References Cited

U.S. PATENT DOCUMENTS

| 5,411,981 A | 5/1995 | Gaillard-Kelly et al. |
| 7,803,826 B2 * | 9/2010 | Tachibana et al. ............ 514/389 |
| 2007/0249697 A1 | 10/2007 | Tachibana et al. |

FOREIGN PATENT DOCUMENTS

| CN | 1063102 | 7/1992 |
| RU | 2152934 | 7/2000 |
| RU | 2285695 | 10/2006 |
| SU | 596165 | 2/1978 |
| WO | WO 02/074751 | 9/2002 |

* cited by examiner

*Primary Examiner* — Kamal Saeed
*Assistant Examiner* — Janet L Coppins
(74) *Attorney, Agent, or Firm* — Hunton & Williams LLP

(57) ABSTRACT

The present application relates to novel imidazolidine-2,4-dione derivatives of the general formula (I), where $R^1$, $R^2$, $R^3$, $R^4$, X, and Y are variables. Said materials have an antiproliferative activity. They are particularly useful for treating pathological conditions and diseases, such as cancer, that are linked to abnormal cell proliferation. The invention also relates to pharmaceutical compositions containing said materials and to the use thereof for preparing a drug.

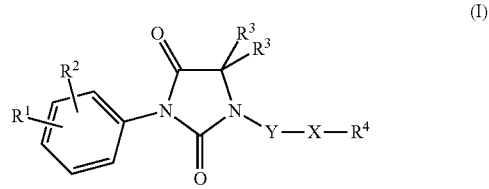

(I)

21 Claims, 2 Drawing Sheets

IMIDAZOLIDINE-2,4-DIONE DERIVATIVES, AND USE THEREOF AS A CANCER DRUG

This application is a national stage of filing of PCT/FR2010/000315, filed Apr. 16, 2010, the subject matter of which is incorporated herein in its entirety. This application further claims priority to FR 0901865, filed Apr. 17, 2009, the subject matter of which is incorporated herein in its entirety.

FIELD OF THE INVENTION

A subject of the present application is novel imidazolidine-2,4-dione derivatives. These products have an anti-proliferative activity. They are particularly useful for treating the pathological states and the diseases linked to an abnormal proliferation cell such as cancers. The invention also relates to the pharmaceutical compositions containing said products and their use for the preparation of a medicament.

STATE OF THE ART

Detailed Description of the Invention

Nowadays, cancer still constitutes one of the major causes of death despite there being numerous molecules on the medicament market.

It is therefore necessary to identify more powerful novel molecules allowing a better anti-tumour response, specifically by a good inhibitory activity on the proliferation of tumour cell colonies.

Such molecules are therefore particularly useful for treating the pathological states linked to an abnormal proliferation cell. They can therefore be used for the treatment of tumours or cancers, for example, those of the oesophagus, the stomach, the intestines, the rectum, the oral cavity, the pharynx, the larynx, the lung, the colon, the breast, the cervix uteri, the corpus endometrium, the ovaries, the prostate, the testes, the bladder, the kidneys, the liver, the pancreas, the bones, the connective tissues, the skin such as melanomas, the eyes, the brain and the central nervous system, as well as cancer of the thyroid gland, leukaemia, Hodgkin's disease, non-Hodgkin's lymphomas, multiple myelomas and other cancers.

It is of particular interest to find therapies for hormone-dependent cancers, for tumours expressing androgen receptors, for cancers of the breast and prostate.

The use of the anti-androgens in prostate cancer is based on their property of entering into competition with the natural agonists of the androgen receptor. However, the efficacy of these anti-androgens appears to be limited over time, in the end treatments are failing patients. Several hypotheses regarding this failure have been developed showing an agonist activity in place of an antagonist activity of these molecules (Veldscholte J, Berrevoets C A, Brinkmann A O, Grootegoed J A, Mulder E. Biochemistry 1992 Mar. 3; 31(8): 2393-9). For example, nilutamide is capable of stimulating the growth of human prostate cancer cells in culture. In addition to these experimental indications, clinical data also support this deleterious role of the anti-androgens (Akimoto S.; Antiandrogen withdrawal syndrome Nippon Rinsho. 1998 August; 56(8):2135-9. Paul R, Breul J. Antiandrogen withdrawal syndrome associated with prostate cancer therapies: incidence and clinical significance Drug Saf. 2000 November; 23(5):381-90).

Furthermore, obtaining pure anti-androgen compounds does not appear to be straightforward, thus the work of K. Tachibana et al. in *Bioorg. Med. Chem.* 15 (2007) 174-185 as well as that of Cantin et al. in *The Journal of Biological Chemistry*, 282, 42, (2007) 30910-30919, show that compounds with very similar chemical structures, having a ligand-based pharmacophore of the androgen receptors can lead to agonist as well as antagonist biological activities.

In this case the Applicant has identified compounds showing an anti-proliferative activity for the prostatic tumour which surprisingly does not show agonist activity at concentrations where the nilutamide behaves as an agonist. This difference in the novel compounds' behaviour with respect to proliferation compared with that of nilutamide is supported by their ability to induce the disappearance of androgen receptors in their protein form. Nilutamide has no effect on this receptor level.

The properties of these novel molecules must allow better management of prostate cancer avoiding the failure of current anti-androgens.

Moreover, the compounds of the present invention can also be used for treating pathologies linked to the presence of androgen receptors such as for example benign prostatic hyperplasia, prostamegaly, acne, androgenic alopecia, hirsutism etc.

SUMMARY OF THE INVENTION

A subject of the invention is therefore the compounds of general formula (I)

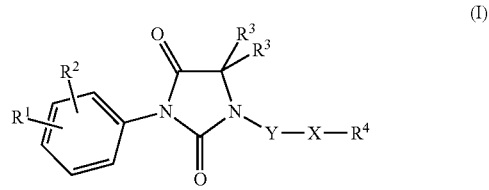

in racemic or enantiomeric form or any combinations of these forms and in which, $R^1$ and $R^2$ represent independently a halogen atom, or an alkyl, haloalkyl, alkoxy, cyano, nitro, amino, alkylamino, dialkylamino, $-NR^8-CO-R^5$, $-NR^8-SO_2-R^5$, $-NR^8-CO-(CH_2)_n-NR^6R^7$, $-NR^8-SO_2-(CH_2)_n-NR^6R^7$ or $-CO-NH_2$ radical;

n represents an integer chosen from 0, 1, 2, 3, 4, 5 and 6;

$R^5$ represents an alkyl, aryl, or heteroaryl radical;

$R^6$ and $R^7$ represent independently a hydrogen atom, an alkyl or alkyloxycarbonyl radical;

$R^8$ represents a hydrogen atom or an alkyl radical;

$R^3$ represents an alkyl radical or a hydrogen atom; or the two $R^3$ radicals form together with the carbon atom to which they are attached a cycloalkyl radical comprising 3 to 6 members;

$R^4$ represents a haloalkyl radical with 2 to 10 carbon atoms;

Y represents a linear or branched alkylene chain with 2 to 14 carbon atoms, this chain being able to be saturated or unsaturated, and being able to contain one or more additional —O— members;

X represents $-S-$, $-SO-$, $-SO_2-$, $-S=N(R^9)-$ or $-S(O)=N(R^9)-$, $R^9$ represents a hydrogen atom or a haloalkylcarbonyl radical or a pharmaceutically acceptable salt thereof.

Preferably, Y represents a saturated linear alkylene chain with 2 to 14 carbon atoms.

Preferably, $R^1$ represents a halogen atom, or an alkyl, alkoxy, cyano, nitro, amino, alkylamino, dialkylamino, $-NR^8-CO-R^5$, $-NR^8-SO_2-R^5$, $-NR^8-CO-$ $(CH_2)_n$—$NR^6$, $R^7$, —$NR^8$—$SO_2$—$(CH_2)_n$—$NR^6$, $R^7$, or —CO—$NH_2$ radical; $R^2$ represents a halogen atom, an alkyl or haloalkyl radical.

Preferably, $R^2$ represents a hydrogen atom.
Preferably, $R^8$ represents a hydrogen atom.
Preferably, $R^5$ represents an alkyl radical.
Preferably, $R^3$ represents an alkyl radical.
Preferably, $R^4$ represents a haloalkyl radical comprising 4 to 6 carbon atoms and 3 to 9 fluorine atoms; and Y represents an alkylene chain with 5 to 10 carbon atoms.

Preferably, n represents an integer chosen from 0, 1, 2, 3 and 4. Preferably, n is equal to 0 or 1. Preferably, n is equal to 0. Preferably, n is equal to 1. According to an alternative, n is equal to 2. According to an alternative, n is equal to 3.

Preferably, $R^1$ is in para position.
Preferably, $R^2$ is in meta position.
Preferably, $R^1$ represents a cyano, nitro, amino, —$NR^8$—CO—$R^5$, —$NR^8$—$SO_2$—$R^5$, —$NR^8$—CO—$(CH_2)_n$—$NR^6R^7$, —$NR^8$—$SO_2$—$(CH_2)_n$—$NR^6$, $R^7$, or —CO—$NH_2$ radical;
$R^2$ represents an alkyl or haloalkyl radical;
$R^5$ represents an alkyl radical;
$R^6$ and $R^7$ represent independently a hydrogen atom, an alkyl or alkyloxycarbonyl radical;
$R^3$ represents an alkyl radical or the two $R^3$ radicals form together with the carbon atom to which they are attached a cycloalkyl radical comprising 3 to 6 members;
$R^4$ represents a haloalkyl radical comprising 4 to 6 carbon atoms and 3 to 9 fluorine atoms;
n is equal to 0 or 1; and
$R^9$ represents a hydrogen atom or —$COCF_3$.

Preferably, $R^1$ represents a cyano, nitro, amino, —NH—CO—$R^5$, —CO—$NH_2$, —NH—CO—$NHR^6$, —NH—$SO_2$—$NHR^6$ radical;
$R^2$ represents an alkyl or haloalkyl radical
$R^5$ represents an alkyl radical;
$R^6$ represents a hydrogen atom, an alkyl or alkyloxycarbonyl radical;
$R^3$ represents an alkyl radical;
$R^4$ represents a haloalkyl radical comprising 4 to 6 carbon atoms and 3 to 9 fluorine atoms;
And n represents an integer comprised between 5 and 11.

Preferably, $R^1$ represents a cyano, nitro, —$NR^8$—CO—$R^5$, —$NR^8$—$SO_2$—$R^5$, —$NR^8$—CO—$(CH_2)_n NR^6$, $R^7$, —$NR^8$—$SO_2$—$(CH_2)_n$—$NR^6$, $R^7$, or —CO—$NH_2$ radical; n is equal to 0 or 1; $R^5$ represents an alkyl radical, $R^6$ and $R^7$ represent independently a hydrogen atom or an alkyl radical, and $R^2$ represents an alkyl or haloalkyl radical.

Preferably, $R^1$ represents a cyano, nitro, —NH—CO—$R^5$, —CO—$NH_2$, —NH—CO—$NHR^6$, —NH—$SO_2$—$NHR^6$ radical; $R^5$ represents an alkyl radical, $R^6$ represents a hydrogen atom or an alkyl radical, and $R^2$ represents an alkyl or haloalkyl radical.

Preferably, $R^1$ represents a nitro or —$NR^8$—CO—$R^5$ radical in which $R^5$ represents an alkyl radical.

Preferably, $R^1$ represents a nitro or —NH—CO—$R^5$ radical in which $R^5$ represents an alkyl radical.

Preferably, the alkyl radical represents a methyl group and/or the haloalkyl radical represents a trifluoromethyl group, or a radical of molecular formula $C_5H_6F_5$, $C_5H_4F_7$, $C_6H_8F_5$, $C_6H_6F_7$ or $C_6H_4F_9$.

Preferably, Y represents an alkylene chain with 9 to 10 carbon atoms.

Preferentially, a subject of the present invention is a compound of general formula (I) chosen from:

5,5-dimethyl-3-[4-nitro-3-(trifluoromethyl)phenyl]-1-{9-[(4,4,5,5,5-pentafluoropentypthio]nonyl}imidazolidine-2,4-dione
5,5-dimethyl-3-[4-nitro-3-(trifluoromethyl)phenyl]-1-{9-[(4,4,5,5,5-pentafluoropentyl)sulphinyl]nonyl}imidazolidine-2,4-dione
5,5-dimethyl-3-[4-nitro-3-(trifluoromethyl)phenyl]-1-{9-[(4,4,5,5,5-pentafluoropentyl)sulphonyl]nonyl}imidazolidine-2,4-dione
5,5-dimethyl-3-[4-nitro-3-(trifluoromethyl)phenyl]-1-{5-[(4,4,5,5,5-pentafluoropentyl)thio]pentyl}imidazolidine-2,4-dione
5,5-dimethyl-3-[4-nitro-3-(trifluoromethyl)phenyl]-1-{5-[(4,4,5,5,5-pentafluoropentyl)sulphinyl]pentyl}imidazolidine-2,4-dione
5,5-dimethyl-3-[4-nitro-3-(trifluoromethyl)phenyl]-1-{8-[(4,4,5,5,5-pentafluoropentypthio]octyl}imidazolidine-2,4-dione
5,5-dimethyl-3-[4-nitro-3-(trifluoromethyl)phenyl]-1-{8-[(4,4,5,5,5-pentafluoropentyesulphinyl]octyl}imidazolidine-2,4-dione
5,5-dimethyl-3-[4-nitro-3-(trifluoromethyl)phenyl]-1-{10-[(4,4,5,5,5-pentafluoropentypthio]decyl}imidazolidine-2,4-dione
5,5-dimethyl-3-[4-nitro-3-(trifluoromethyl)phenyl]-1-{10-[(4,4,5,5,5-pentafluoropentyl)sulphinyl]decyl}imidazolidine-2,4-dione
5,5-dimethyl-3-[4-nitro-3-(trifluoromethyl)phenyl]-1-{11-[(4,4,5,5,5-pentafluoropentyethio]undecyl}imidazolidine-2,4-dione
5,5-dimethyl-3-[4-nitro-3-(trifluoromethyl)phenyl]-1-{11-[(4,4,5,5,5-pentafluoropentyl)sulphinyl]undecyl}imidazolidine-2,4-dione
5,5-dimethyl-3-[4-nitro-3-(trifluoromethyl)phenyl]-1-{9-[(4,4,4-trifluorobutyl)thio]nonyl}imidazolidine-2,4-dione
5,5-dimethyl-3-[4-nitro-3-(trifluoromethyl)phenyl]-1-{9-[(4,4,4-trifluorobutyl)sulphinyl]nonyl}imidazolidine-2,4-dione
5,5-dimethyl-3-[4-nitro-3-(trifluoromethyl)phenyl]-1-{9-[(3,3,4,4,5,5,6,6,6-nonafluorohexyl)thio]nonyl}imidazolidine-2,4-dione
5,5-dimethyl-3-[4-nitro-3-(trifluoromethyl)phenyl]-1-{9-[(3,3,4,4,5,5,6,6,6-nonafluorohexyl)sulphinyl]nonyl}imidazolidine-2,4-dione
3-[4-amino-3-(trifluoromethyl)phenyl]-5,5-dimethyl-1-{9-[(4,4,5,5,5-pentafluoropentypthio]nonyl}imidazolidine-2,4-dione
N-[4-(4,4-dimethyl-2,5-dioxo-3-{9-[(4,4,5,5,5-pentafluoropentyl)thio]-nonyl}imidazolidin-1-yl)-2-(trifluoromethyl)phenyl]acetamide
N-[4-(4,4-dimethyl-2,5-dioxo-3-{9-[(4,4,5,5,5-pentafluoropentyl)sulphinyl]-nonyl}imidazolidin-1-yl)-2-(trifluoromethyl)phenyl]acetamide
4-(4,4-dimethyl-2,5-dioxo-3-{9-[(4,4,5,5,5-pentafluoropentylsulphanyl]nonyl}imidazolidin-1-yl)-2-(trifluoromethyl)benzonitrile
4-(4,4-dimethyl-2,5-dioxo-3-{9-[(4,4,5,5,5-pentafluoropentyl)sulphinyl]nonyl}imidazolidin-1-yl)-2-(trifluoromethyl)benzonitrile
4-(4,4-dimethyl-2,5-dioxo-3-{9-[(4,4,5,5,5-pentafluoropentyl)sulphanyl]nonyl}imidazolidin-1-yl)-2-(trifluoromethyl)benzamide
4-(4,4-dimethyl-2,5-dioxo-3-{9-[(4,4,5,5,5-pentafluoropentyl)sulphinyl]nonyl}imidazolidin-1-yl)-2-(trifluoromethyl)benzamide 5,5-dimethyl-3-(3-methyl-4-nitrophenyl)-1-{9-[(4,4,5,5,5-pentafluoro pentyl)sulphanyl]nonyl}imidazolidine-2,4-dione 5,5-dimethyl-3-(3-methyl-4-nitrophenyl)-1-{9-[(4,4,5,5,5-pentafluoro pentyl)sulphinyl]nonyl}imidazolidine-2,4-dione 3-(4-amino-3-methylphenyl)-5,5-dimethyl-1-{9-[(4,4,5,5,5-pentafluoro pentyl)sulphanyl]nonyl}imidazolidine-2,4-dione 3-(4-amino-3-methylphenyl)-5,5-dimethyl-1-{9-[(4,4,5,5,5-pentafluoro pentyl)sulphinyl]nonyl}imidazolidine-2,4-dione 1-[4-(4,4-dimethyl-2,5-dioxo-3-{9-[(4,4,5,5,5-pentafluoropentyl)sulphanyl]nonyl}imidazolidin-1-yl)-2-methylphenyl]-3-(1-methylpropyl)urea 1,4-[4-(4,4-dimethyl-2,5-dioxo-3-{9-[(4,4,5,5,5-pentafluoropentyl)sulphinyl]nonyl}imidazolidin-1-yl)-2-methylphenyl]-3-(1-methylpropyl)urea tert-butyl {[4-(4,4-dimethyl-2,5-dioxo-3-{9-[(4,4,5,5,5-pentafluoropentyl)sulphanyl]nonyl}imidazolidin-1-yl)-2-methylphenyl]sulphamoyl}carbamate N-[4-(4,4-dimethyl-2,5-dioxo-3-{9-[(4,4,5,5,5-pentafluoropentyl)sulphanyl]nonyl}imidazolidin-1-yl)-2-methylphenyl]sulphamide N-[4-(4,4-dimethyl-2,5-dioxo-3-{9-[(4,4,5,5,5-pentafluoropentyl)sulphinyl]nonyl}imidazolidin-1-yl)-2-methylphenyl]sulphamide N-[4-(4,4-dimethyl-2,5-dioxo-3-{9-[(4,4,5,5,5-pentafluoropentyl)sulphonyl]nonyl}imidazolidin-1-yl)-2-methylphenyl]sulphamide 3-[4-amino-3-(trifluoromethyl)phenyl]-5,5-dimethyl-1-{9-[(4,4,5,5,5-pentafluoropentyl)sulphinyl]nonyl}imidazolidine-2,4-dione.

7-[4-nitro-3-(trifluoromethyl)phenyl]-5-{9-[(4,4,5,5,5-pentafluoropentyl)sulphinyl]nonyl}-5,7-diazaspiro[3.4]octane-6,8-dione 5,5-dimethyl-3-[4-nitro-2-(trifluoromethyl)phenyl]-1-{9-[(4,4,5,5,5-pentafluoropentyl)sulphinyl]nonyl}imidazolidine-2,4-dione 5,5-dimethyl-3-[4-nitro-3-(trifluoromethyl)phenyl]-1-[2-(2-{2-[4,4,5,5,5-pentafluoropentyl)sulphanyl]ethoxy}ethoxy)ethyl]imidazolidine-2,4-dione 5,5-dimethyl-3-[4-nitro-3-(trifluoromethyl)phenyl]-1-[2-(2-{2-[(4,4,5,5,5-pentafluoropentyl)sulphanyl]ethoxy}ethoxy)ethyl]imidazolidine-2,4-dione N-[4-{4,4-dimethyl-2,5-dioxo-3-[2-(2-{2-[(4,4,5,5,5-pentafluoropentyl)sulphanyl]ethoxy}ethoxy)ethyl]imidazolidin-1-yl}-2-(trifluoromethyl)phenyl]acetamide N-[4-{4,4-dimethyl-2,5-dioxo-3-[2-(2-{2-[(4,4,5,5,5-pentafluoropentyl)sulphinyl]ethoxy}ethoxy)ethyl]imidazolidin-1-yl}-2-(trifluoromethyl)phenyl]acetamide N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N-methylacetamide N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]methanesulphonamide N-[4-(4,4-dimethyl-2,5-dioxo-3-{9-[(4,4,5,5,5-pentafluoropentyl)sulphanyl]nonyl}imidazolidin-1-yl)-2-(trifluoromethyl)phenyl]-N2,N2-dimethylglycinamide N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N2,N2-dimethylglycinamide N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N2,N2-dimethylglycinamide hydrochloride N-[(1Z)-(9-{5,5-dimethyl-3-[4-nitro-3-(trifluoromethyl)phenyl]-2,4-dioxoimidazolidin-1-yl}nonyl)(4,4,5,5,5-pentafluoropentyl)-4-sulphanylidene]-2,2,2-trifluoroacetamide N-[(9-{5,5-dimethyl-3-[4-nitro-3-(trifluoromethyl)phenyl]-2,4-dioxoimidazolidin-1-yl}nonyl)(oxido)(4,4,5,5,5-pentafluoropentyl)-4-sulphanylidene]-2,2,2-trifluoroacetamide 5,5-dimethyl-3-[4-nitro-3-(trifluoromethyl)phenyl]-1-{9-[S-(4,4,5,5,5-pentafluoropentyl)sulphonimidoyl]nonyl}imidazolidine-2,4-dione.

Preferably, the compound of formula (I) is chosen from:

5,5-dimethyl-3-[4-nitro-3-(trifluoromethyl)phenyl]-1-{9-[(4,4,5,5,5-pentafluoropentyethio]nonyl}imidazolidine-2,4-dione 5,5-dimethyl-3-[4-nitro-3-(trifluoromethyl)phenyl]-1-{9-[(4,4,5,5,5-pentafluoropentyl)sulphinyl]nonyl}imidazolidine-2,4-dione 5,5-dimethyl-3-[4-nitro-3-(trifluoromethyl)phenyl]-1-{9-[(4,4,5,5,5-pentafluoropentyl)sulphonyl]nonyl}imidazolidine-2,4-dione 5,5-dimethyl-3-[4-nitro-3-(trifluoromethyl)phenyl]-1-{5-[(4,4,5,5,5-pentafluoropentyl)thio]pentyl}imidazolidine-2,4-dione 5,5-dimethyl-3-[4-nitro-3-(trifluoromethyl)phenyl]-1-{5-[(4,4,5,5,5-pentafluoropentyl)sulphinyl]pentyl}imidazolidine-2,4-dione 5,5-dimethyl-3-[4-nitro-3-(trifluoromethyl)phenyl]-1-{8-[(4,4,5,5,5-pentafluoropentypthio]octyl}imidazolidine-2,4-dione 5,5-dimethyl-3-[4-nitro-3-(trifluoromethyl)phenyl]-1-{8-[(4,4,5,5,5-pentafluoropentyl)sulphinyl]octyl}imidazolidine-2,4-dione 5,5-dimethyl-3-[4-nitro-3-(trifluoromethyl)phenyl]-1-{10-[(4,4,5,5,5-pentafluoropentypthio]decyl}imidazolidine-2,4-dione 5,5-dimethyl-3-[4-nitro-3-(trifluoromethyl)phenyl]-1-{10-[(4,4,5,5,5-pentafluoropentyl)sulphinyl]decyl}imidazolidine-2,4-dione 5,5-dimethyl-3-[4-nitro-3-(trifluoromethyl)phenyl]-1-{11-[(4,4,5,5,5-pentafluoropentyl)thio]undecyl}imidazolidine-2,4-dione 5,5-dimethyl-3-[4-nitro-3-(trifluoromethyl)phenyl]-1-{11-[(4,4,5,5,5-pentafluoropentyl)sulphinyl]undecyl}imidazolidine-2,4-dione 5,5-dimethyl-3-[4-nitro-3-(trifluoromethyl)phenyl]-1-{9-[(4,4,4-trifluorobutyl)thio]nonyl}imidazolidine-2,4-dione 5,5-dimethyl-3-[4-nitro-3-(trifluoromethyl)phenyl]-1-{9-[(4,4,4-trifluorobutyl)sulphinyl]nonyl}imidazolidine-2,4-dione 5,5-dimethyl-3-[4-nitro-3-(trifluoromethyl)phenyl]-1-{9-[(3,3,4,4,5,5,6,6,6-nonafluorohexyl)thio]nonyl}imidazolidine-2,4-dione 5,5-dimethyl-3-[4-nitro-3-(trifluoromethyl)phenyl]-1-{9-[(3,3,4,4,5,5,6,6,6-nonafluorohexyl)sulphinyl]nonyl}imidazolidine-2,4-dione 3-[4-amino-3-(trifluoromethyl)phenyl]-5,5-dimethyl-1-{9-[(4,4,5,5,5-pentafluoropentyl)thio]nonyl}imidazolidine-2,4-dione N-[4-(4,4-dimethyl-2,5-dioxo-3-{9-[(4,4,5,5,5-pentafluoropentypthio]-nonyl}imidazolidin-1-yl)-2-(trifluoromethyl)phenyl]acetamide N-[4-(4,4-dimethyl-2,5-dioxo-3-{9-[(4,4,5,5,5-pentafluoropentyl)sulphinyl]-nonyl}imidazolidin-1-yl)-2-(trifluoromethyl)phenyl]acetamide 4-(4,4-dimethyl-2,5-dioxo-3-{9-[(4,4,5,5,5-pentafluoropentylsulphanyl]nonyl}imidazolidin-1-yl)-2-(trifluoromethyl)benzonitrile 4-(4,4-dimethyl-2,5-dioxo-3-{9-[(4,4,5,5,5-pentafluoropentyl)sulphinyl]nonyl}imidazolidin-1-yl)-2-(trifluoromethyl)benzonitrile 4-(4,4-dimethyl-2,5-dioxo-3-{9-[(4,4,5,5,5-pentafluoropentyl)sulphanyl]nonyl}imidazolidin-1-yl)-2-(trifluoromethyl)benzamide 4-(4,4-dimethyl-2,5-dioxo-3-{9-[(4,4,5,5,5-pentafluoropentyl)sulphinyl]nonyl}imidazolidin-1-yl)-2-(trifluoromethyl)benzamide 5,5-dimethyl-3-(3-methyl-4-nitrophenyl)-1-{9-[(4,4,5,5,5-pentafluoro pentyl)sulphanyl]nonyl}imidazolidine-2,4-dione 5,5-dimethyl-3-(3-methyl-4-nitrophenyl)-1-{9-[(4,4,5,5,5-pentafluoro pentyl)sulphinyl]nonyl}imidazolidine-2,4-dione 3-(4-amino-3-methylphenyl)-5,5-dimethyl-1-{9-[(4,4,5,5,5-pentafluoro pentyl)sulphanyl]nonyl}imidazolidine-2,4-dione 3-(4-amino-3-methylphenyl)-5,5-dimethyl-1-{9-[(4,4,5,5,5-pentafluoro pentyl)sulphinyl]nonyl}imidazolidine-2,4-dione 1-[4-(4,4-dimethyl-2,5-dioxo-3-{9-[(4,4,5,5,5-pentafluoropentyl)sulphanyl]nonyl}imidazolidin-1-yl)-2-methylphenyl]-3-(1-methylpropyl)urea 1-[4-(4,4-dimethyl-2,5-dioxo-3-{9-[(4,4,5,5,5-pentafluoropentyl)sulphinyl]nonyl}imidazolidin-1-yl)-2-methylphenyl]-3-(1-methylpropyl)urea tert-butyl {[4-(4,4-dimethyl-2,5-dioxo-3-{9-[(4,4,5,5,5-pentafluoropentyl)sulphanyl]nonyl}imidazolidin-1-yl)-2-methylphenyl]sulphamoyl}carbamate N-[4-(4,4-dimethyl-2,5-dioxo-3-{9-[(4,4,5,5,5-pentafluoropentyl)sulphanyl]nonyl}imidazolidin-1-yl)-2-methylphenyl]sulphamide N-[4-(4,4-dimethyl-2,5-dioxo-3-{9-[(4,4,5,5,5-pentafluoropentyl)sulphinyl]nonyl}imidazolidin-1-yl)-2-methylphenyl]sulphamide N-[4-(4,4-dimethyl-2,5-dioxo-3-{9-[(4,4,5,5,5-pentafluoropentyl)sulphonyl]nonyl}imidazolidin-1-yl)-2-methylphenyl]sulphamide 3-[4-amino-3-(trifluoromethyl)phenyl]-5,5-dimethyl-1-{9-[(4,4,5,5,5-pentafluoropentyl)sulphinyl]nonyl}imidazolidine-2,4-dione.

Even more preferably, a subject of the present invention is a compound of general formula (I) chosen from:

5,5-dimethyl-3-[4-nitro-3-(trifluoromethyl)phenyl]-1-{9-[(4,4,5,5,5-pentafluoropentyl)sulphinyl]nonyl}imidazolidine-2,4-dione 5,5-dimethyl-3-[4-nitro-3-(trifluoromethyl)phenyl]-1-{10-[(4,4,5,5,5-pentafluoropentyl)sulphinyl]decyl}imidazolidine-2,4-dione 5,5-dimethyl-3-[4-nitro-3-(trifluoromethyl)phenyl]-1-{9-[((4,4,4-trifluorobutyl)thio]nonyl}imidazolidine-2,4-dione 5,5-dimethyl-3-[4-nitro-3-(trifluoromethyl)phenyl]-1-{9-[((4,4,4-trifluorobutyl)sulphinyl]nonyl}imidazolidine-2,4-dione N-[4-(4,4-dimethyl-2,5-dioxo-3-{9-[(4,4,5,5,5-pentafluoropentyl)sulphinyl]-nonyl}imidazolidin-1-yl)-2-(trifluoromethyl)phenyl]acetamide N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N2,N2-dimethylglycinamide N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N2,N2-dimethylglycinamide hydrochloride.

Preferably, the compound is chosen from
5,5-dimethyl-3-[4-nitro-3-(trifluoromethyl)phenyl]-1-{9-[(4,4,5,5,5-pentafluoropentyl)sulphinyl]nonyl}imidazolidine-2,4-dione;

5,5-dimethyl-3-[4-nitro-3-(trifluoromethyl)phenyl]-1-{10-[(4,4,5,5,5-pentafluoropentyl)sulphinyl]decyl}imidazolidine-2,4-dione;

5,5-dimethyl-3-[4-nitro-3-(trifluoromethyl)phenyl]-1-{9-[((4,4,4-trifluorobutyl)thio]nonyl}imidazolidine-2,4-dione;

5,5-dimethyl-3-[4-nitro-3-(trifluoromethyl)phenyl]-1-{9-[((4,4,4-trifluorobutyl)sulphinyl]nonyl}imidazolidine-2,4-dione;

N-[4-(4,4-dimethyl-2,5-dioxo-3-{9-[(4,4,5,5,5-pentafluoropentyl)sulphinyl]-nonyl}imidazolidin-1-yl)-2-(trifluoromethyl)phenyl]acetamide.

Preferably, the compound is N-[4-(4,4-dimethyl-2,5-dioxo-3-{9-[(4,4,5,5,5-pentafluoropentyl)sulphinyl]-nonyl}imidazolidin-1-yl)-2-(trifluoromethyl)phenyl]acetamide.

Preferably, the compound is N-[4-(4,4-dimethyl-2,5-dioxo-3-{9-[(4,4,5,5,5-pentafluoropentyesulphinyl]nonyl}imidazolidin-1-yl)-2-(trifluoromethyl)phenyl]-N2,N2-dimethylglycinamide.

Preferably, the compound is N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N2,N2-dimethylglycinamide hydrochloride.

A subject of the invention is also a process for the preparation of a compound of formula (I) as defined previously, characterized in that it comprises obtaining compounds of general formula (I.1) (compound of general formula (I) in which X represents the sulphur atom),

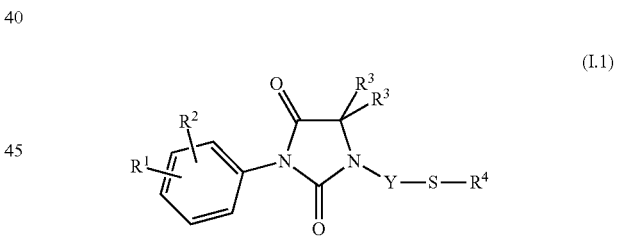

(I.1)

in which $R^1$, $R^2$, $R^3$, $R^4$ and Y are as defined previously, either by condensation of the hydantoin derivatives of general formula (II)

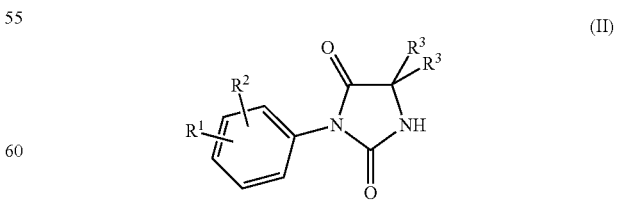

(II)

in which $R^1$, $R^2$, and $R^3$ are as defined previously, in the presence of a strong base at a temperature comprised between 25 and 60° C., in an anhydrous polar solvent, with the mesylate derivatives of general formula (III),

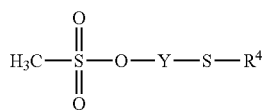
(III)

in which R⁴ and Y are as defined previously,
or by treatment of the thiobenzoyl derivatives of general formula (V),

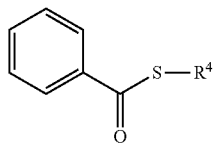
(V)

in which R⁴ is as defined previously, by an alcoholate in a polar protic solvent followed by
addition of the halogenated derivative of general formula (IV),

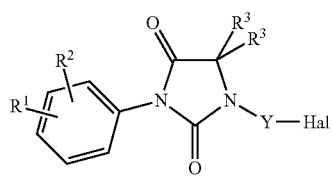
(IV)

in which $R^1$, $R^2$, $R^3$ and Y are as defined previously, in solution in a polar solvent.

Preferably, the process comprises moreover a stage of oxidation of the compounds of general formula (I.1) to sulphoxide of general formula (I.2) (compound of general formula (I) in which X represents the —SO— radical),

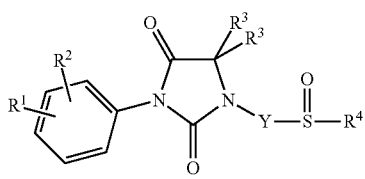
(I.2)

in which $R^1$, $R^2$, $R^3$, $R^4$ and Y are as defined previously.

Preferably, the process for the preparation of a compound of formula (I), comprises moreover a stage of oxidation of the sulphoxide derivatives of general formula (I.2) to the sulphones of general formula (I.3) (compound of general formula (I) in which X represents the —SO₂— group),

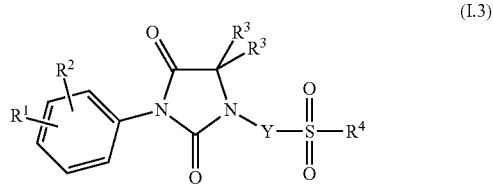
(I.3)

in which $R^1$, $R^2$, $R^3$, $R^4$ and Y are as defined previously.

A subject of the invention is also one of the following compounds as an intermediate:

1-(5-iodopentyl)-5,5-dimethyl-3-[4-nitro-3-(trifluoromethyl)phenyl]imidazolidine-2,4-dione 1-(8-iodooctyl)-5,5-dimethyl-3-[4-nitro-3-(trifluoromethyl)phenyl]imidazolidine-2,4-dione 1-(9-bromononyl)-5,5-dimethyl-3-[4-nitro-3-(trifluoromethyl)phenyl]imidazolidine-2,4-dione 4-[3-(9-bromononyl)-4,4-dimethyl-2,5-dioxoimidazolidin-1-yl]-2-(trifluoromethyl)benzonitrile 5,5-dimethyl-3-(3-methyl-4-nitrophenyl)imidazolidine-2,4-dione 1-(9-bromononyl)-5,5-dimethyl-3-(3-methyl-4-nitrophenyl)imidazolidine-2,4-dione.

A subject of the invention is also one of the compounds of formula (I) as a medicament.

A subject of the invention is also the pharmaceutical compositions containing, as active ingredient, at least one compound of formula (I) as defined previously, in combination with a pharmaceutically acceptable support.

A subject of the invention is also the use of a compound of formula (I) for the preparation of a medicament intended to treat cancers.

Preferably, the medicament is intended to treat a hormone-dependent cancer.

Preferably, the medicament is intended to treat a cancer expressing androgen receptors Preferably, the medicament is intended to treat a cancer of the breast or the prostate.

DETAILED DESCRIPTION OF EMBODIMENTS OF THE INVENTION

Figure 1:
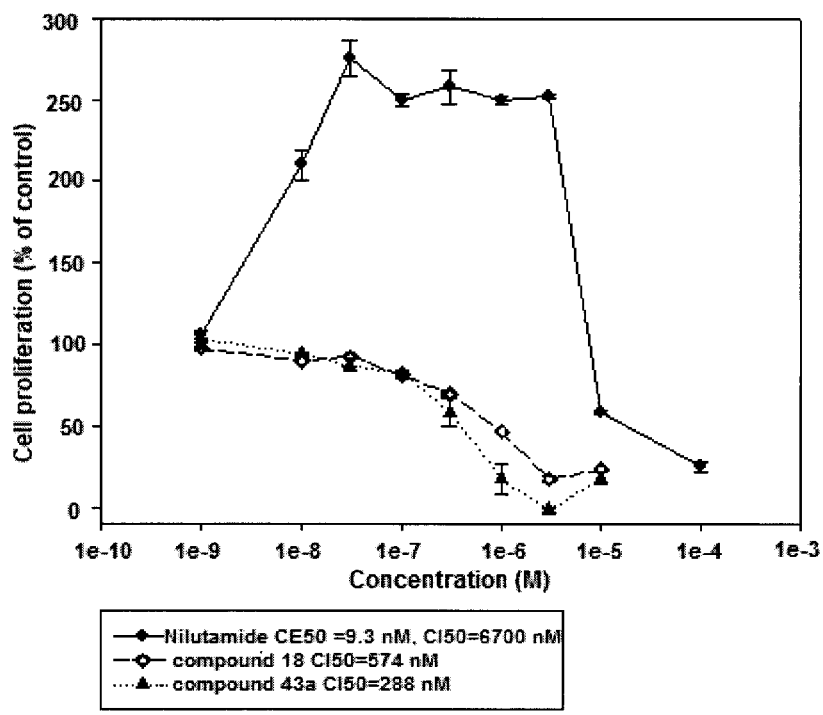
FIG. 1 represents the effect of compounds 18 and 43a on the proliferation of LNCaP cells cultured in medium without steroids.
Figure 2:
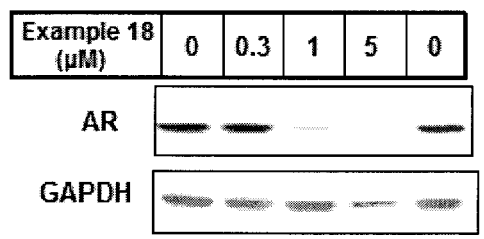
FIGS. 2 and 3 represent the effects of compounds 18 and 43a on the reduction in the protein expression of the androgen receptor.
Figure 3:
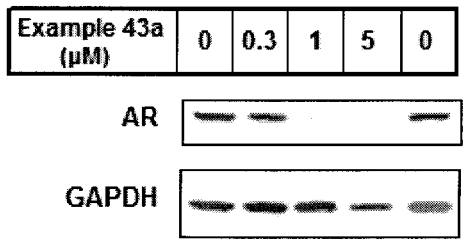
Figure 4:
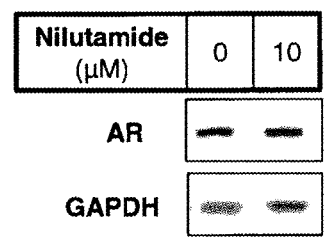
FIG. 4 represents the effect of nilutamide on the reduction in the protein expression of the androgen receptor.

Therefore a subject of the invention is the compounds of general formula (I)

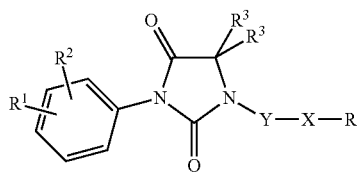

(I)

in racemic or enantiomeric form or any combinations of these forms.

$R^1$ and $R^2$ represent independently a halogen atom, or an alkyl, haloalkyl, alkoxy, cyano, nitro, amino, alkylamino, dialkylamino, —$NR^8$—CO—$R^5$, —$NR^8$—$SO_2$—$R^5$, —$NR^8$—CO—$(CH_2)_n$—$NR^6,R^7$, —$NR^8$—$SO_2$—$(CH_2)_n$—$NR^6R^7$ or —CO—$NH_2$ radical.

n represents an integer comprised between 0 and 6.

$R^5$ represents an alkyl, aryl, or heteroaryl radical. Preferably, $R^5$ is an alkyl radical.

$R^6$ and $R^7$ represent independently a hydrogen atom, an alkyl or alkyloxycarbonyl radical.

$R^8$ represents a hydrogen atom or an alkyl radical. Preferably, $R^8$ represents a hydrogen atom.

$R^3$ represents an alkyl radical or a hydrogen atom. Alternatively, the two $R^3$ radicals form, together with the carbon atom to which they are attached, a cycloalkyl radical comprising 3 to 6 members.

$R^4$ represents a haloalkyl radical with 2 to 10 carbon atoms.

Y represents an alkylene chain with 2 to 14 carbon atoms. The Y chain can be linear or branched. This chain can be saturated or unsaturated. It can contain one or more additional —O— members.

X represents —S—, —SO—, —$SO_2$—, —S=N($R^9$)— or —S(O)=N($R^9$)—. $R^9$ represents a hydrogen atom or a haloalkylcarbonyl radical.

The compounds of formula (I) can be in the form of a pharmaceutically acceptable salt.

By pharmaceutically acceptable salt, is meant in particular addition salts of inorganic acids such as hydrochloride, hydrobromide, sulphate, phosphate, diphosphate and nitrate or organic acids such as acetate, maleate, fumarate, tartrate, succinate, citrate, lactate, methanesulphonate, benzenesulphonate, p-toluenesulphonate, pamoate and stearate. Also included within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

In the definitions indicated above, the expression halogen (or halo) represents the fluoro, chloro, bromo or iodo radical, preferably chloro, fluoro or bromo. More preferentially, the expression halogen (or halo) represents a fluoro radical.

Unless otherwise specified, the term alkyl within the meaning of the present invention represents a linear or branched alkyl radical comprising between 1 and 12 carbon atoms such as the methyl, ethyl, propyl, isopropyl, butyl, isobutyl, sec-butyl and tert-butyl, pentyl or amyl, isopentyl, neopentyl, hexyl or isohexyl, heptyl, octyl, nonyl, decyl, undecyl or dodecyl radicals. Preferentially the alkyl radical is a $(C_1-C_6)$ alkyl radical, i.e. representing an alkyl radical having 1 to 6 carbon atoms as defined above, or a $(C_1-C_4)$alkyl radical representing an alkyl radical having 1 to 4 carbon atoms such as for example the methyl, ethyl, propyl, isopropyl, butyl, isobutyl, sec-butyl and tert-butyl radicals.

The term alkyl in the expressions alkoxy (or alkyloxy), alkylamino, dialkylamino, haloalkyl or alkoxycarbonyl (or alkyloxycarbonyl) represents an alkyl radical as defined above.

More particularly, by haloalkyl, is meant an alkyl radical at least one (and optionally all) of the hydrogen atoms of which is replaced by a halogen atom (halo) such as for example, and preferentially trifluoromethyl or the radicals of molecular formula $C_5H_6F_5$, $C_5H_4F_7$, $C_6H_8F_5$, $C_6H_6F_7$ or $C_6H_4F_9$.

The term haloalkyl in the expression haloalkylcarbonyl represents a haloalkyl radical as defined above.

By cycloalkyl unless otherwise specified, is meant a saturated cyclic carbon radical comprising 3 to 6 members such as the cyclopropyl, cyclobutyl, cyclopentyl or cyclohexyl.

Within the meaning of the present invention, the aryl radicals can be of mono or polycyclic aromatic type. The monocyclic aryl radicals can be chosen from the phenyl, tolyl, xylyl, mesityl, cumenyl radicals and preferably phenyl. The polycyclic aryl radicals can be chosen from the naphthyl, anthryl, phenanthryl, fluorenyl radicals. They can be optionally substituted by one or more identical or different radicals such as alkyl, haloalkyl, alkoxy, alkoxycarbonyl, alkylcarbonyloxy, halo, cyano, nitro, aryl, aryloxy, aryloxycarbonyl, or arylcarbonyloxy.

Within the meaning of the present invention, the term heteroaryl designates an unsaturated aromatic ring comprising one or more identical or different heteroatoms chosen from N, O and S such as furyl, thienyl isoxazolyl, benzothiadiazolyl, pyridinyl, oxazolyl, pyrazolyl, pyrimidinyl or quinoxalyl.

By linear or branched, saturated or unsaturated alkylene chain with 2 to 14 carbon atoms is meant for example a methyl, ethyl, propyl, isopropyl, butyl, isobutyl, sec-butyl and tert-butyl, pentyl or amyl, isopentyl, neopentyl, hexyl or isohexyl, heptyl, octyl, nonyl, decyl, undecyl, dodecyl, ethene, propene, butene, pentene, hexene, heptene, octene, nonene, decylene, undecylene, dodecylene, or the buta-1,3-diene chain.

By pharmaceutically acceptable salt, is meant in particular addition salts of inorganic acids such as hydrochloride, hydrobromide, sulphate, phosphate, diphosphate and nitrate or organic acids such as acetate, maleate, fumarate, tartrate, succinate, citrate, lactate, methanesulphonate, benzenesulphonate, p-toluenesulphonate, pamoate and stearate. Also included within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

A subject of the invention is also a process for the preparation of a compound of formula (I) as defined previously. The compounds of general formula (I.1) (compound of general formula (I) in which X represents the sulphur atom),

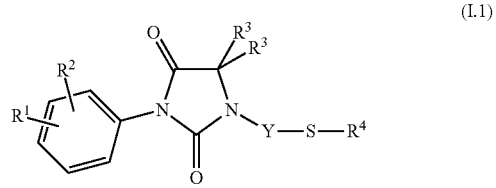

(I.1)

in which $R^1$, $R^2$, $R^3$, $R^4$ and Y are as defined previously, can be obtained by condensation of the hydantoin derivatives of general formula (II)

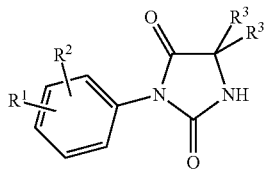

(II)

in which R¹, R², and R³ are as defined previously with the mesylate derivatives of general formula (III),

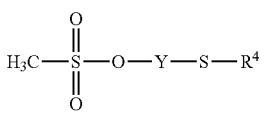

(III)

in which R⁴ and Y are as defined previously.

The condensation is carried out in the presence of a strong base. The condensation is carried out at a temperature comprised between 25 and 60° C. The solvent is preferably an anhydrous polar solvent.

The compounds of general formula (I.1) can also be obtained (i) by treatment of the thiobenzoyl derivatives of general formula (V),

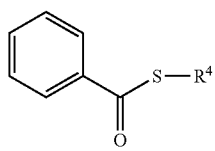

(V)

in which R⁴ is as defined previously, with an alcoholate in a polar protic solvent, followed by addition of the halogenated derivative of general formula (IV),

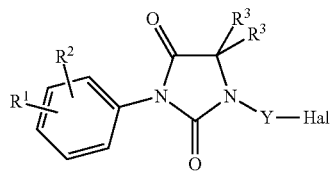

(IV)

in which R¹, R², R³ and Y are as defined previously, in solution in a polar solvent;

Preferably, the compounds of general formula (I.1) are converted, by oxidation, to the sulphoxide of general formula (I.2) (compound of general formula (I) in which X represents the —SO— radical),

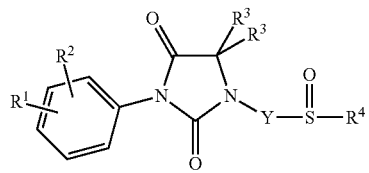

(I.2)

in which R¹, R², R³, R⁴ and Y are as defined previously.

Preferably, the sulphoxide derivatives of general formula (I.2) can be converted, by oxidation, to the sulphones of general formula (I.3) (compound of general formula (I) in which X represents the —SO₂— group),

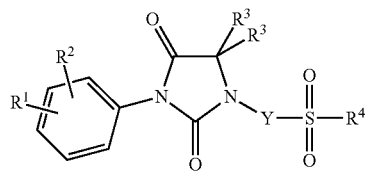

(I.3)

in which R¹, R², R³, R⁴ and Y are as defined previously.

The compounds of general formula (I) according to the invention can be prepared according to the synthesis route represented in Diagram 1 below. The compounds of general formula (I) in which R¹, R², R³, R⁴ and Y are as described above can be obtained according to two different approaches depending on the ease of access to the intermediates. The condensation of the hydantoin derivatives of general formula (II) with the mesylate derivatives of general formula (III) (prepared according to an experimental protocol described in WO 2005077968) is carried out in the presence of a base, such as for example NaH, preferably by heating between 25 and 60° C. and for a period of 5 to 15 hours in an anhydrous polar solvent, such as for example THF or DMF, in order to produce the compounds of general formula (I.1). Alternatively, the compounds of general formula (I.1) can be prepared by treatment of the thiobenzoyl derivatives of general formula (V) (prepared according to an experimental protocol described in WO 2005077968) by an alcoholate, such as for example tBuO⁻K⁺, in solution in a polar protic solvent, preferentially MeOH, for a period of 30 minutes to 2 hours, before addition of the halogenated derivative of general formula (IV) in solution in a polar solvent, such as for example MeOH. The reaction is generally carried out at about 20° C. and for a time which can vary from 10 to 24 hours. The oxidation of the thioether group of the compounds of general formula (I.1) to sulphoxide of general formula (I.2) is carried out in the presence of a sub-equivalent quantity of Oxone in a mixture of solvents such as THF and water at a temperature of 20° C. and for a period of time of 15 to 30 minutes.

The conversion of the sulphoxide derivatives of general formula (I.2) to sulphones of general formula (I.3) is also carried out in a mixture of solvent such as THF and water in the presence of Oxone. Three equivalents of the oxidizing agent and a reaction time of 3 to 5 hours are generally necessary to carry out the total conversion.

Diagram 1

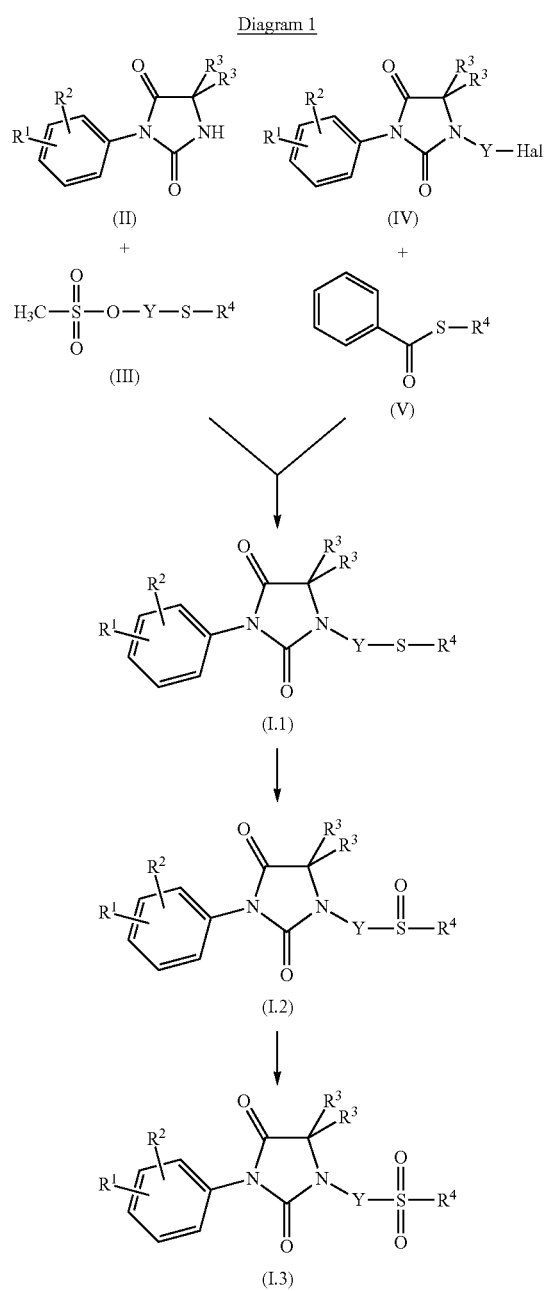

The sulphanilidene derivatives of general formula (I.2) in which $R^2$, $R^3$, $R^4$, $R^9$ and Y are as described above, are prepared from the thio alkyl derivatives of general formula (I.1), diagram I-a. The reaction is carried out under experimental conditions similar to those described by C. Bolm et al. in *Organic Letters* 2004, vol. 6, No. 17, 1305-1307. The reaction is carried out by reacting an acetamide derivative $R^9$—$NH_2$ and the thio alkyl compound of general formula (Id) in the presence of an oxidizing agent such as for example magnesium oxide, at a temperature comprised between 20° C. and 30° C. (preferably 25° C.), in an inert solvent such as for example tetrahydrofuran or a chlorinated solvent and in particular dichloromethane and for a duration of several hours. The derivative of general formula (I.2)-a is then reacted at a temperature comprised between 20° C. and 30° C. (preferably 25° C.), in the presence of a mineral base and in particular potassium hydroxide in an inert solvent such as for example tetrahydrofuran, an alcoholated solvent and in particular methanol and for a duration of several hours in order to produce the compound of general formula (I-2).

Diagram I-a

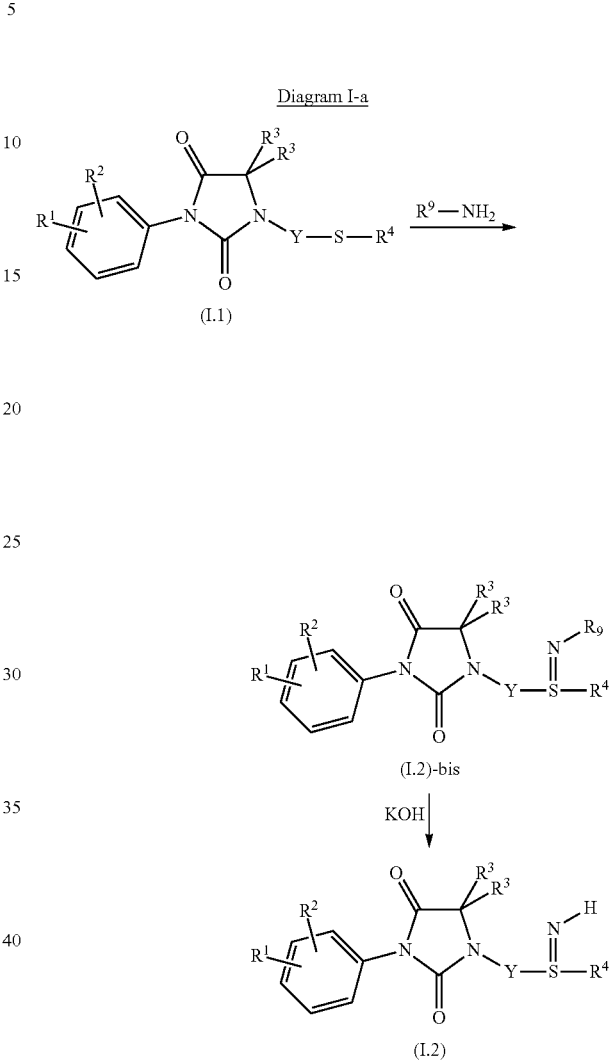

The sulphonimide derivatives of general formula (I.3) in which $R^2$, $R^3$, $R^4$, $R^9$ and Y are as described above, are prepared from the sulphoxide derivatives of general formula (I.2), diagram I-b. The reaction is carried out under experimental conditions similar to those described by C. Bolm et al. in *Organic Letters* 2004, vol. 6, N° 17, 1305-1307. The reaction is carried out by reacting an acetamide derivative $R^9$—$NH_2$ and a sulphoxide compound of general formula (I.2) in the presence of an oxidizing agent such as for example magnesium oxide, at a temperature comprised between 20° C. and 30° C. (preferably 25° C.), in an inert solvent such as for example tetrahydrofuran or a chlorinated solvent and in particular dichloromethane and for a duration of several hours. The derivative of general formula (I.3)-b is then reacted at a temperature comprised between 20° C. and 30° C. (preferably 25° C.), in the presence of a mineral base and in particular of potassium carbonate in an inert solvent such as for example tetrahydrofuran or an alcoholated solvent and in particular methanol and for a duration of several hours in order to obtain the compound of formula (I.3).

Diagram I-b

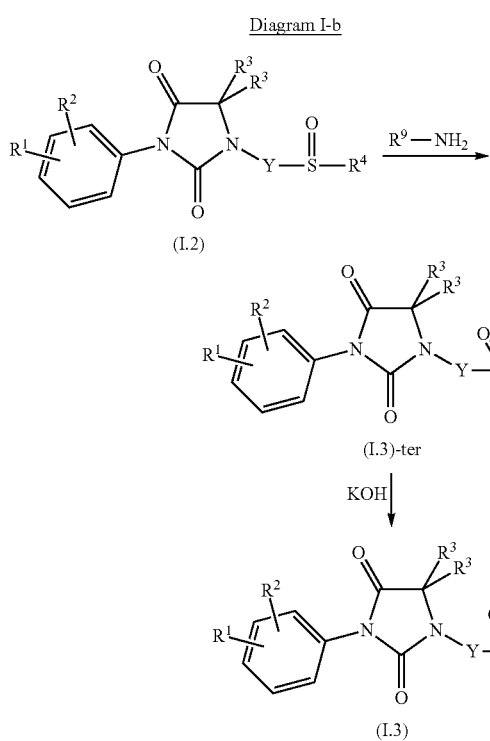

A) Preparation of the Compounds of General Formula (I.1) in which $R^1$ is an Optionally Substituted Amino Group:

A.1) Preparation of the Aniline Derivatives:

In the particular case where $R^1$ is a nitro group, $R^2$, $R^3$ and $R^4$ being as described above, the preparation of the aniline derivatives of general formula $(I.1)_{A1}$ is represented in Diagram A1. The reduction of the nitro groups of the compounds of general formula (I.1) is carried out using $SnCl_2$, $2H_2O$ (*J. Heterocyclic Chem.* 1987, 24, 927-930; *Tetrahedron Letters* 1984, 25 (8), 839-842) by heating the reaction mixture under reflux, in a solvent such as ethyl acetate, for several hours.

Diagram A1

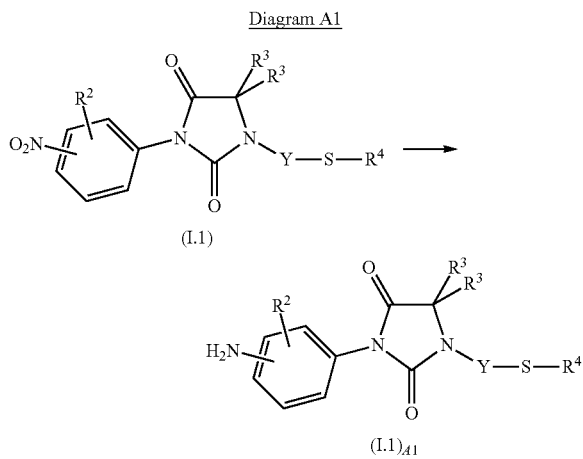

A.2) Preparation of the Acetamide Derivatives:

The acetamide derivatives of general formula $(I.1)_{A2}$ in which $R^2$, $R^3$, $R^4$ and $R^5$ are as described above, are accessible in one stage from the aniline derivatives of general formula $(I.1)_{A1}$, Diagram A2. The acylation reaction can be carried out using an excess of acid chloride of general formula $R^5$—COCl, for example acetyl chloride, or an anhydride of $(R^5$—$CO)_2O$ type, such as acetic anhydride. The reaction is generally carried out at about 20° C., in an anhydrous solvent such as for example dichloromethane, and for a duration of a few hours.

Diagram A2

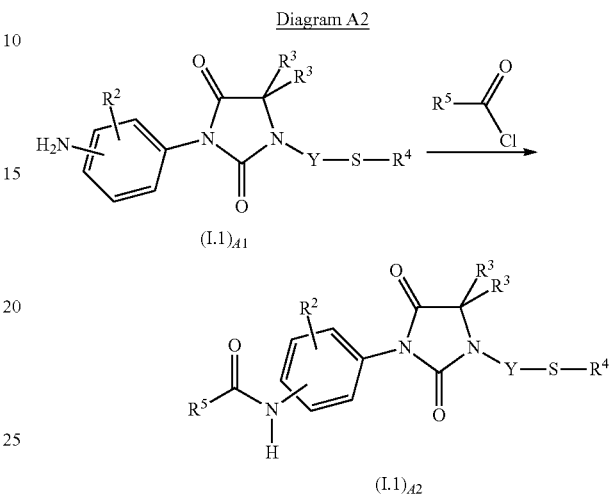

The synthesis of the intermediates of general formula (I.1) A2a, Diagram A2a, in which $R^2$, $R^3$, $R^4$, $R^5$, $R^8$ and Y are as described above is carried out by nucleophilic substitution of a halogen atom of the halogenated reagent of general formula $R^8$—Hal, by the anion of the acetamide of general formula (I.1)A2 generated in the presence of a base such as, for example NaH, in a polar aprotic solvent such as DMF or DMSO. The reaction is generally carried out at a temperature varying from 20 to 30° C. and for a duration of 1 to 5 hours.

Diagram A2a

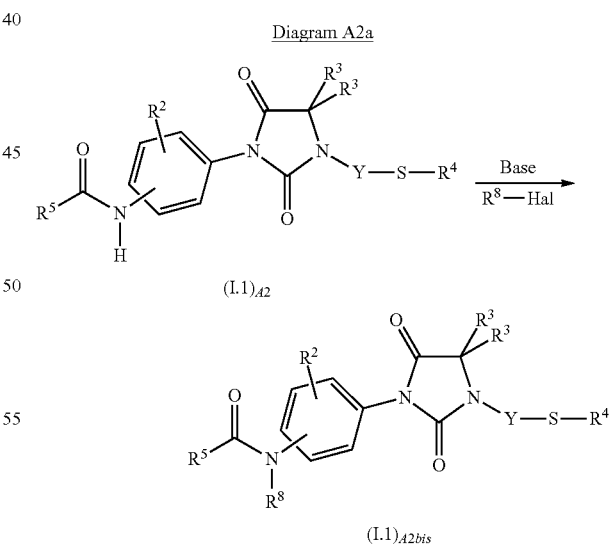

A.3) Preparation of the Urea Derivatives:

The urea derivatives of general formula $(I.1)_{A3}$ in which $R^2$, $R^3$, $R^4$ and $R^6$ are as described above, are prepared in one stage from the aniline derivatives of general formula $(I.1)_{A1}$, Diagram A3. The reaction is carried out in the presence of an isocyanate derivative $R^6$—N=C=O, by heating the reaction mixture to a temperature comprised between 70 and 120° C., generally in an inert solvent such as, for example, a chlorinated solvent and in particular 1,2-dichloroethane and for a duration of several hours.

Diagram A3

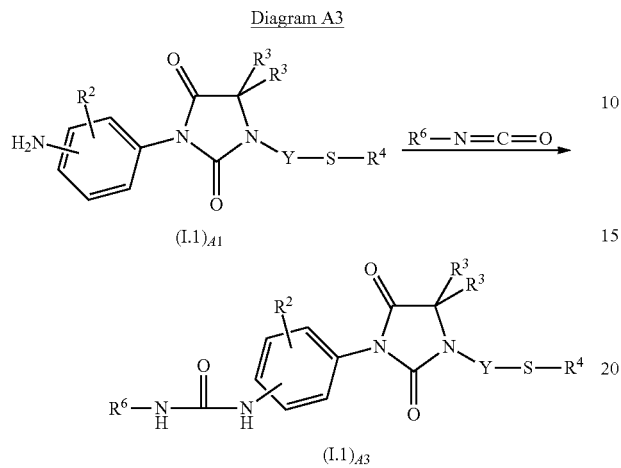

A.4) Preparation of the Sulphamide Derivatives:

The sulphamide derivatives of general formula $(I.1)_{A3}$ in which $R^2$, $R^3$, $R^4$ and $R^6$ are as described above, are prepared from the aniline derivatives of general formula $(I.1)_{A1}$, Diagram A4. The reaction is carried out under experimental conditions similar to those described in WO2007125197.

Diagram A4

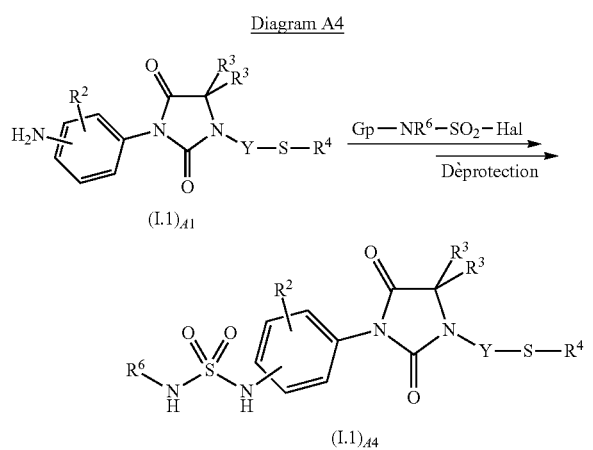

A.5) Preparation of the Sulphonamide Derivatives:

The sulphonamide derivatives of general formula $(I.1)_{A5}$ in which $R^2$, $R^3$, $R^4$, $R^5$ and Y are as described above, are prepared from the aniline derivatives of general formula $(I.1)_{A1}$, Diagram A5. The reaction is carried out under experimental conditions similar to those described by G. H. Chu et al. in *Bioorg. Med. Chem. Lett.* 2007, 17, 1951-1955. The reaction is carried out by reacting a sulphonyl chloride derivative $R^5$—$SO_2$—Cl and the aniline compound of general formula $(I.1)_{A1}$ in which $R^2$, $R^3$, $R^4$, have been defined previously, at a temperature comprised between 20° C. and 30° C. (preferably 25° C.), in an inert solvent such as for example tetrahydrofuran, a chlorinated solvent and in particular 1,2-dichloroethane and for a duration of several hours. The disulphonamide derivative of general formula (I.1)A5-1 is then reacted at a temperature comprised between 20° C. and 30° C. (preferably 25° C.), in the presence of a mineral base and in particular lithium hydroxide in an inert solvent such as for example tetrahydrofuran, an alcoholated solvent and in particular methanol and for a duration of several hours.

Diagram A5

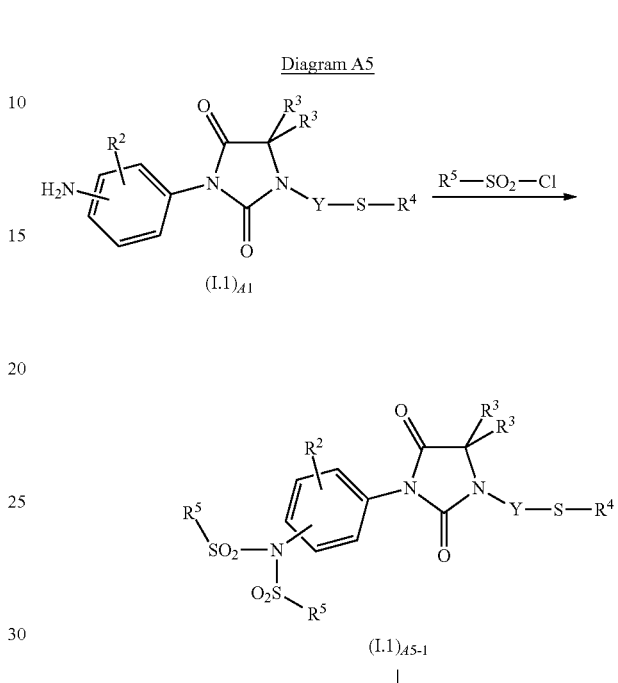

B) Syntheses for Preparing the Compounds of General Formula (I.1) in which $R^1$ is a Carboxamide Group:

B.1) Preparation of the Carboxamide Derivatives:

The carboxamide derivatives of general formula $(I.1)_{B1}$ in which $R^2$, $R^3$ and $R^4$ are as described above, are prepared in one stage from the nitrile derivatives of general formula (I.1), diagram B1. The hydrolysis reaction is carried out in a mixture of trifluoroacetic acid and sulphuric acid, followed by a treatment in aqueous medium (*J. Org. Chem.* 2005, 70 (5), 1926-1929).

Diagram B1

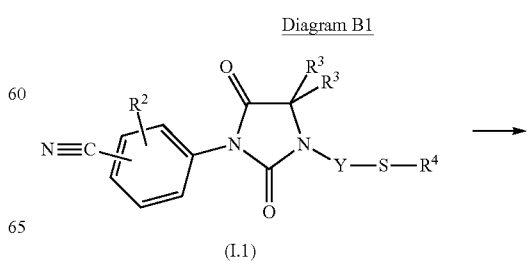

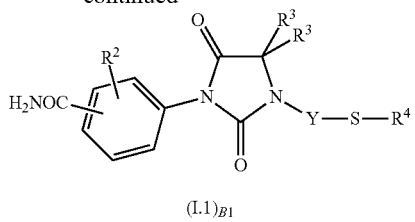

(I.1)$_{B1}$

C) Preparation of the Intermediates of General Formula (II):

The synthesis of the arylhydantoin intermediates of general formula (II) in which $R^1$, $R^2$ and $R^3$ are as described above can be carried out according to the strategies described in the diagrams below:

C.1) Preparation of the Arylhydantoins by Condensation:

The synthesis of the arylhydantoin of general formula (II), Diagram B1, can be carried out by nucleophilic substitution of the fluorine atom borne by the aromatic ring of the compound of general formula (II)$_1$ by the anion of the hydantoin of general formula (II)$_2$ generated in the presence of a base such as, for example K$_2$CO$_3$. The reaction is carried out by heating at a temperature comprised between 65 and 140° C. and in a polar aprotic solvent such as, for example, DMF or DMSO. The temperature and the reaction time are a function of the nucleofugal character of the fluorine atom which is highly dependent on the nature of Ie and $R^2$. The hydantoins of general formula 002 that are not commercially available can be prepared according to the methods described in the literature (e.g. *J. Med. Chem.* 1984, 27 (12), 1663-8). The hydantoins of general formula (II)$_2$ that are not commercially available can be prepared according to the methods described in the literature (e.g. *J. Med. Chem.* 1984, 27 (12), 1663-8).

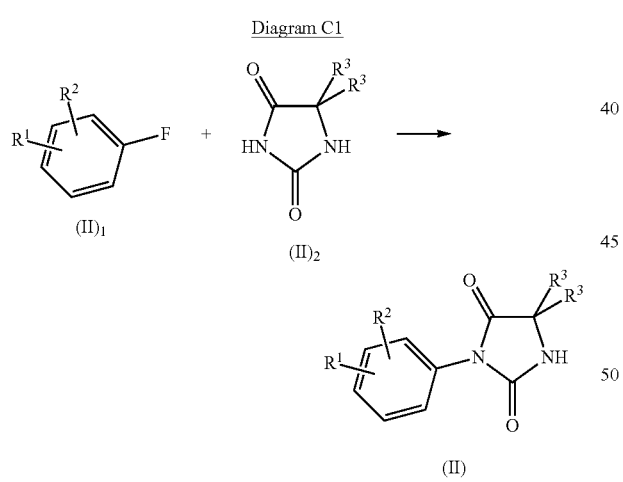

In the cases where Wet $R^2$ are not sufficiently electro-attractive to promote the aromatic nucleophilic substitution described in Diagram C1, an approach by coupling between an aryl boronic acid and the hydantoin of general formula (II)$_2$ in the presence of copper acetate can be envisaged (*Synlett* 2006, 14, 2290-2) in order to obtain the compounds of general formula (II).

C.2) Preparation of the Arylhydantoins by Construction of the Hydantoin Ring from Arylisocyanate:

Access to the hydantoins of general formula (II) is carried out, in this case, according to a protocol described in *Bioorg. Med. Chem. Lett.* 2004, 14, 5285.

C.3) Preparation of the Arylhydantoins by Construction of the Hydantoin Ring from the Isocyanates of Aminoesters:

Alternatively, the arylhydantoins of general formula (II) can be synthesized from the isocyanate of aminoesters as described in *Eur. J. Med. Chem.* 1984, 19 (3), 261.

D) Preparation of the Intermediates of General Formula (IV):

The synthesis of the intermediates of general formula (IV), Diagram D1, in which $R^1$, $R^1$, $R^3$ and Y are as described above is carried out by nucleophilic substitution of a halogen atom of the dihalogenated reagent of general formula Hal-(CH$_2$)-Hal, by the anion of the hydantoin of general formula (II) generated in the presence of a base such as, for example, NaH in a polar aprotic solvent such as DMF or DMSO. The reaction is generally carried out at a temperature varying from 20 to 60° C. and for a duration of 1 to 15 hours.

Diagram D1

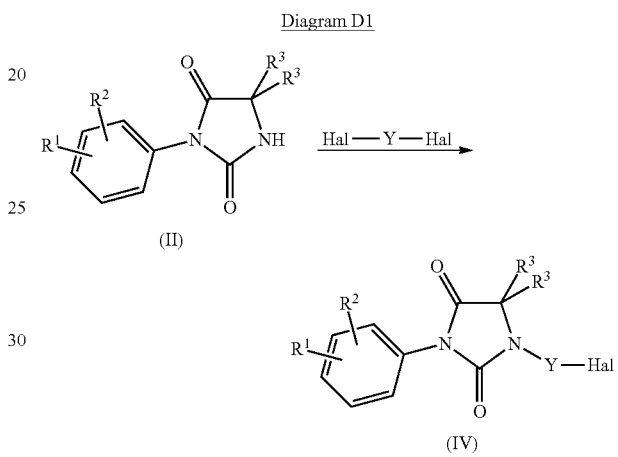

Thus, a subject of the invention is also a process for the preparation of a compound of formula (I) as defined above, this process comprising obtaining compounds of general formula (I.1) (compound of general formula (I), in which X represents the sulphur atom),

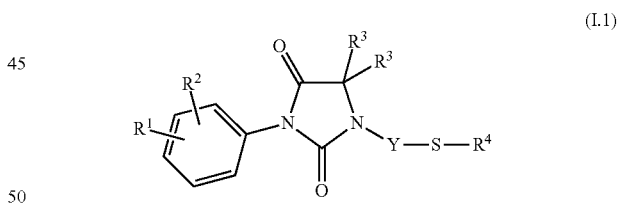

in which $R^1$, $R^2$, $R^3$, $R^4$ and Y are as defined previously, either by condensation of the hydantoin derivatives of general formula (II),

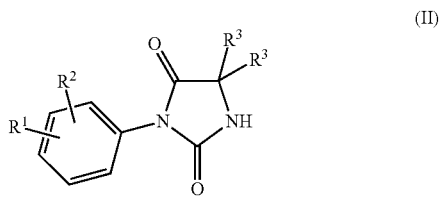

in which $R^1$, $R^2$, and $R^3$ are as defined previously, in the presence of a strong base at a temperature comprised between 25 and 60° C., in an anhydrous polar solvent, with the mesylate derivatives of general formula (III),

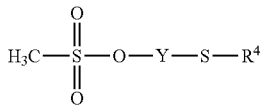
(III)

in which $R^4$ and Y are as defined previously, or by the treatment of the thiobenzoyl derivatives of general formula (V),

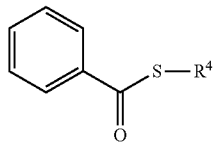
(V)

in which $R^4$ is as defined previously, by an alcoholate in a polar protic solvent followed by addition of the halogenated derivative of general formula (IV),

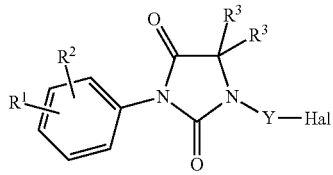
(IV)

in which $R^1$, $R^2$, $R^3$ and Y are as defined previously, in solution in a polar solvent;

compounds of general formula (I.1) the thioether group of which is oxidized to sulphoxide of general formula (I.2) (compound of general formula (I) in which X represents the —SO— radical),

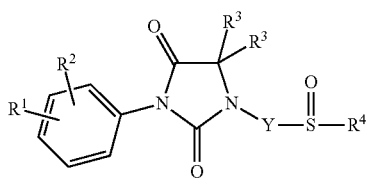
(I.2)

in which $R^1$, $R^2$, $R^3$, $R^4$ and Y are as defined previously, the sulphoxide derivatives of general formula (I.2) which are oxidized to sulphones of general formula (I.3) (compound of general formula (I) in which X represents the —SO$_2$— group),

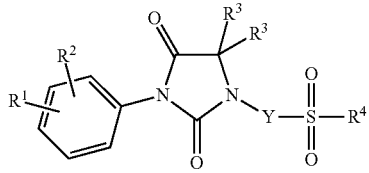
(I.3)

in which $R^1$, $R^2$, $R^3$, $R^4$ and Y are as defined previously.

Preferentially, the oxidations mentioned above take place in the presence of Oxone®.

The salification of the compounds of formula (I) can be carried out by any method known to a person skilled in the art. For example, the salification can be carried out by the addition of a base or an acid, for example, sodium hydroxide, potassium hydroxide, or hydrochloric acid.

According to a variant, the subject of the invention is one of the following compounds, as an intermediate:

1-(5-iodopentyl)-5,5-dimethyl-3-[4-nitro-3-(trifluoromethyl)phenyl]imidazolidine-2,4-dione 1-(8-iodooctyl)-5,5-dimethyl-3-[4-nitro-3-(trifluoromethyl)phenyl]imidazolidine-2,4-dione 1-(9-bromononyl)-5,5-dimethyl-3-[4-nitro-3-(trifluoromethyl)phenyl]imidazolidine-2,4-dione 4-(4,4-dimethyl-2,5-dioxoimidazolidin-1-yl)-2-(trifluoromethyl)benzonitrile 4-[3-(9-bromononyl)-4,4-dimethyl-2,5-dioxoimidazolidin-1-yl]-2-(trifluoromethyl)benzonitrile 5,5-dimethyl-3-(3-methyl-4-nitrophenyl)imidazolidine-2,4-dione 1-(9-bromononyl)-5,5-dimethyl-3-(3-methyl-4-nitrophenyl)imidazolidine-2,4-dione.

The compounds of formula (I) according to the present invention have useful pharmacological properties. In fact, it has been discovered that the compounds of formula (I) of the present invention have an anti-tumour (anti-cancer) activity, and more particularly an inhibitory activity on the cell proliferation of the cells expressing androgen receptors such as the LnCAP type prostatic cells. Thus, the compounds of the present invention can be used in different therapeutic applications. They can advantageously be used for the treatment of cancers, particularly hormone-dependent cancers, cancers expressing androgen receptors and more particularly breast and prostate cancers. An illustration of the pharmacological properties of the compounds of the invention will be found hereafter in the experimental part.

Therefore, a subject of the present application is also the compounds of formula (I) as defined previously as medicaments.

Also, a subject of the present application is the compounds of formula (I) as defined previously as medicaments intended to treat the proliferative diseases, preferentially cancers, very preferentially hormone-dependent cancers or cancers expressing androgen receptors, or also prostate and breast cancers and very preferentially prostate cancers.

A subject of the present application is also pharmaceutical compositions containing, as active ingredient, at least one compound of formula (I) as defined above, in combination with a pharmaceutically acceptable support.

A subject of the present application is also the use of a compound of formula (I) according to the present invention, for the preparation of an anti-tumour medicament.

A subject of the present application is also the use of a compound of formula (I) according to the present invention, for the preparation of a medicament intended to inhibit cell proliferation.

A subject of the present application is also the use of a compound of formula (I) according to the present invention, for the preparation of a medicament intended to treat proliferative diseases, preferentially cancers, very preferentially hormone-dependent cancers or cancers expressing androgen receptors, or prostate and breast cancers and very preferentially prostate cancers.

The pharmaceutical composition can be in the form of a solid, for example powders, granules, tablets, gelatin capsules. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, as well as their mixtures, in varying proportions, in water added to pharmaceutically acceptable oils or fats. The sterile liquid compositions can be used for intramuscular, intraperitoneal or sub-cutaneous injections and the sterile compositions can also be administered by intravenous route.

All the technical and scientific terms used in the present text have the meaning known to a person skilled in the art. Moreover, all the patents (or patent applications) as well as the other bibliographical references are incorporated by way of reference

EXPERIMENTAL PART

Following the definitions of the variables $R^1$, $R^2$, $R^3$, X, n and $R^4$, the compounds according to the invention can be prepared according to the different methods described above.

The examples are presented in order to illustrate the above procedures and should in no event be considered as a limit to the scope of the invention.

Example 1

5,5-dimethyl-3-[4-nitro-3-(trifluoromethyl)phenyl]-1-{9-[(4,4,5,5,5-pentafluoropentyl)thio]nonyl}imidazolidine-2,4-dione NaH (at 60%) (44 mg, 1.1 mmole), is added under argon to a solution of 5,5-dimethyl-3-[4-nitro-3-(trifluoromethyl)phenyl]-imidazolidine-2,4-dione (317 mg, 1 mmole) in anhydrous DMF (8 ml). A release of gas accompanies the change in colour of the reaction medium which becomes orange. Stirring is maintained for 1 hour at 23° C. before adding 9-[(4,4,5,5,5-pentafluoropentyl)-thio]nonyl methanesulphonate (prepared according to an experimental protocol described in WO 2005077968) (332 mg, 0.8 mmole). After reaction for 15 hours, the reaction medium is poured into water (25 ml) and extracted with AcOEt (2×25 ml). The organic phases are combined and washed successively with water (25 ml) and salt water (25 ml). After drying over $Na_2SO_4$, the organic solution is filtered and concentrated under vacuum. The evaporation residue is purified on a silica column (eluent: $CH_2Cl_2$/AcOEt: 1/1 to 0/1). The expected compound is obtained in the form of a pale yellow oil with a yield of 72% (364 mg).

$^1$H NMR 400 MHz (DMSO-$d_6$) δ: 8.32 (d, 1H, Ph); 8.20 (d, 1H, Ph); 8.07 (dd, 1H, Ph); 3.29 (m, 2H, $NCH_2$); 2.57 (m, 2H, $SCH_2$); 2.48 (m, 2H, $SCH_2$); 2.28 (m, 2H, $CH_2$); 1.76 (m, 2H, $CH_2$); 1.61 (m, 2H, $CH_2$); 1.50 (m, 2H, $CH_2$); 1.46 (s, 6H, 2×$CH_3$); 1.30 (m, 10H, 5×$CH_2$).

Example 2

5,5-dimethyl-3-[4-nitro-3-(trifluoromethyl)phenyl]-1-{9-[(4,4,5,5,5-pentafluoropentyl)sulphinyl]nonyl}imidazolidine-2,4-dione Oxone® (211 mg, 0.34 mmole) and water (10 ml) are added to a solution of the compound described in Example 1 (364 mg, 0.57 mmole) in THF (75 ml). The reaction mixture is stirred for 20 minutes, the time necessary for the complete conversion of the starting product, and then poured into water (100 ml). The compound is extracted with AcOEt (2×75 ml), the organic phases are combined and washed with salt water. After drying over $Na_2SO_4$ the organic solution is filtered and concentrated under vacuum. The evaporation residue is purified on a silica column (eluent: $CH_2Cl_2$/AcOEt: 1/1 to 1/4). The expected compound is obtained in the form of a colourless oil with a yield of 86% (321 mg).

$^1$H NMR 400 MHz (DMSO-$d_6$) δ: 8.42 (d, 1H, Ph); 8.30 (d, 1H, Ph); 8.17 (dd, 1H, Ph); 3.39 (m, 2H, $NCH_2$); 2.88 (m, 4H, $CH_2S(=O)CH_2$); 2.48 (m, 21-1, $CH_2$); 2.02 (m, 2H, $CH_2$); 1.72 (m, 4H, 2×$CH_2$); 1.56 (s, 6H, 2×$CH_3$); 1.51 (m, 2H, $CH_2$); 1.42 (m, 8H, 4×$CH_2$).

Example 3

5,5-dimethyl-3-[4-nitro-3-(trifluoromethyl)phenyl]-1-{9-[(4,4,5,5,5-pentafluoropentyl)sulphonyl]nonyl}imidazolidine-2,4-dione Oxone® (566 mg, 0.93 mmole) is added to a solution of the compound of Example 2 (200 mg, 0.31 mmole) in THF (6 ml). The reaction mixture is completed with water (3 ml) and stirred at 23° C. for 3 h 30, the time necessary for the total conversion of the starting product. The mixture is then poured into water (25 ml) and extracted with AcOEt (2×25 ml). After decantation, the organic phases are combined and washed with salt water (20 ml), dried over $Na_2SO_4$, filtered and concentrated to dryness under vacuum. The evaporation residue is purified on a silica column (eluent: Heptane/AcOEt: 1/1 to 3/7). The expected compound is obtained in the form of a colourless oil with a yield of 89% (185 mg).

$^1$H NMR 400 MHz (DMSO-$d_6$) δ: 8.28 (d, 1H, Ph); 8.15 (d, 1H, Ph); 8.04 (dd, 1H, Ph); 3.24 (m, 2H, $NCH_2$); 3.15 (m, 2H, $CH_2S(=O)_2$); 3.05 (m, 2H, $CH_2S(=O)_2$); 2.32 (m, 2H, $CH_2$); 1.87 (m, 2H, $CH_2$); 1.59 (m, 4H, 2×$CH_2$); 1.41 (s, 6H, 2×$CH_3$); 1.35 (m, 2H, $CH_2$); 1.24 (m, 8H×$CH_2$).

Example 4

5,5-dimethyl-3-[4-nitro-3-(trifluoromethyl)phenyl]-1-{5-[(4,4,5,5,5-pentafluoropentyl)thio]pentyl}imidazolidine-2,4-dione 4.1) 1-(5-iodopentyl)-5,5-dimethyl-3-[4-nitro-3-(trifluoromethyl)phenyl]imidazolidine-2,4-dione NaH (to 60%) (65 mg, 1.6 mmole) is added under argon to a solution of 5,5-dimethyl-3-[4-nitro-3-(trifluoromethyl)phenyl]-imidazolidine-2,4-dione (500 mg, 1.6 mmole) in anhydrous DMF (20 ml). A gaseous release accompanies the change of colour of the reaction medium which becomes orange. The stirring is maintained for 1 hour at 23° C. before adding, without dilution, the 1,5-diiodopentane (350 μl, 2.4 mmoles). After reaction for 15 hours, the reaction medium is poured into a saturated aqueous solution of $NH_4Cl$ (25 ml) and extracted with AcOEt (2×25 ml). The organic phases are combined and washed successively with water (25 ml) and salt water (25 ml). After drying over $Na_2SO_4$, the organic solution is filtered and concentrated under vacuum. The evaporation residue is purified on a silica column (eluent: Heptane/AcOEt:7/3 to 6/4). The expected compound is obtained in the form of a colourless oil with a yield of 47% (380 mg).

$^1$H NMR 400 MHz (DMSO-$d_6$) δ: 8.32 (d, 1H, Ph); 8.20 (d, 1H, Ph); 8.07 (dd, 1H, Ph); 3.29 (m, 4H, 2×$CH_2$); 1.81 (m, 2H, $CH_2$); 1.65 (m, 2H, $CH_2$); 1.47 (s, 6H, 2×$CH_3$); 1.41 (m, 2H, $CH_2$).

4.2) 5,5-dimethyl-3-[4-nitro-3-(trifluoromethyl)phenyl]-1-{5-[(4,4,5,5,5-pentafluoropentyl)thio]pentyl}imidazolidine-2,4-dione tBuO$^-$K$^+$ (124 mg, 1.11 mmole) is added under argon to a solution of S-(4,4,5,5,5-pentafluoropentyl)benzene-carbothioate (prepared according to an experimental protocol described in WO 2005077968) (221 mg, 0.74 mmole) in MeOH (10 ml) and stirring is maintained for 30 minutes at 23° C. Intermediate 4.1 (380 mg, 0.74 mmole) in solution in MeOH (10 ml) is then added in one go. After stirring for 24 hours, the reaction mixture is poured into water (25 ml) and extracted with AcOEt (2×25 ml). After decantation, the organic phases are combined and washed with water (20 ml) and salt water (20 ml), dried over $Na_2SO_4$, filtered and concentrated to dryness under vacuum. The evaporation residue is purified on a silica column (eluent: Heptane/AcOEt: 7/3 to 6/4). The expected compound is obtained in the form of a colourless oil with a yield of 75% (320 mg).

$^1$H NMR 400 MHz (DMSO-$d_6$) δ: 8.32 (d, 1H, Ph); 8.20 (d, 1H, Ph); 8.07 (dd, 1H, Ph); 3.30 (m, 2H, N$CH_2$); 2.59 (m, 2H, S$CH_2$); 2.50 (m, 2H, S$CH_2$); 2.29 (m, 2H, $CH_2$); 1.76 (m, 2H, $CH_2$); 1.63 (m, 2H, $CH_2$); 1.55 (m, 2H, $CH_2$); 1.46 (s, 6H, 2×$CH_3$); 1.41 (m, 2H, $CH_2$).

Example 5

5,5-dimethyl-3-[4-nitro-3-(trifluoromethyl)phenyl]-1-{5-[(4,4,5,5,5-pentafluoropentyl)sulphinyl]pentyl}imidazolidine-2,4-dione The experimental protocol used is the same as that described for the synthesis of the compound of Example 2, the compound of Example 4 replacing the compound of Example 1. 136 mg of a white solid is obtained (73%). Melting point: 95-96° C.

$^1$H NMR 400 MHz (DMSO-$d_6$) δ: 8.32 (d, 1H, Ph); 8.20 (d, 1H, Ph); 8.07 (dd, 1H, Ph); 3.33 (m, 2H, N$CH_2$); 2.80 (m, 2H, S(=O)$CH_2$); 2.76 (m, 2H, S(=O)$CH_2$); 2.37 (m, 2H, $CH_2$); 1.92 (m, 2H, $CH_2$); 1.67 (m, 4H, 2×$CH_2$); 1.47 (m, 8H, (2×$CH_3$)+$CH_2$).

Example 6

5,5-dimethyl-3-[4-nitro-3-(trifluoromethyl)phenyl]-1-{8-[(4,4,5,5,5-pentafluoropentyl)thio]octyl}imidazolidine-2,4-dione

6.1) 1-(8-iodooctyl)-5,5-dimethyl-3-[4-nitro-3-(trifluoromethyl)phenyl]imidazolidine-2,4-dione The experimental protocol used is the same as that described for the synthesis of intermediate 4.1, 1,8-diiodooctane replacing 1,5-diiodopentane. The expected compound is obtained in the form of a pale yellow oil with a yield of 44% (229 mg).

$^1$H NMR 400 MHz (DMSO-$d_6$) δ: 8.32 (d, 1H, Ph); 8.20 (d, 1H, Ph); 8.07 (dd, 1H, Ph); 3.28 (m, 4H, $CH_2$I+N$CH_2$); 1.73 (m, 2H, $CH_2$); 1.63 (m, 2H, $CH_2$); 1.46 (s, 6H, 2×$CH_3$); 1.30 (m, 8H, 4×$CH_2$).

6.2) 5,5-dimethyl-3-[4-nitro-3-(trifluoromethyl)phenyl]-1-{8-[(4,4,5,5,5-pentafluoropentyl)thio]octyl}imidazolidine-2,4-dione The experimental protocol used is the same as that described for the synthesis of the compound of Example 4, intermediate 6.1 replacing intermediate 4.1. A pale yellow oil is obtained with a yield of 78%.

$^1$H NMR 400 MHz (DMSO-$d_6$) δ: 8.32 (d, 1H, Ph); 8.20 (d, 1H, Ph); 8.07 (dd, 1H, Ph); 3.28 (m, 2H, N$CH_2$); 2.58 (m, 2H, S$CH_2$); 2.47 (m, 2H, S$CH_2$); 2.27 (m, 2H, $CH_2$); 1.76 (m, 2H, $CH_2$); 1.62 (m, 2H, $CH_2$); 1.51 (m, 2H, $CH_2$); 1.46 (s, 6H, 2×$CH_3$); 1.30 (m, 8H, 4×$CH_2$).

Example 7

5,5-dimethyl-3-[4-nitro-3-(trifluoromethyl)phenyl]-1-{8-[(4,4,5,5,5-pentafluoropentyl)sulphinyl]octyl}imidazolidine-2,4-dione The experimental protocol used is the same as that described for the synthesis of the compound of Example 2, Example 6 replacing the compound of Example 1. 61 mg of a pale yellow oil is obtained (64%).

$^1$H NMR 400 MHz (DMSO-$d_6$) δ: 8.32 (d, 1H, Ph); 8.20 (d, 1H, Ph); 8.07 (dd, 1H, Ph); 3.28 (m, 2H, N$CH_2$); 2.74 (m, 4H, $CH_2$S(=O)$CH_2$); 2.37 (m, 2H, $CH_2$); 1.90 (m, 2H, $CH_2$); 1.63 (m, 4H, 2×$CH_2$); 1.46 (s, 6H, 2×$CH_3$); 1.40 (m, 2H, $CH_2$); 1.32 (m, 6H, 3×$CH_2$).

Example 8

5,5-dimethyl-3-[4-nitro-3-(trifluoromethyl)phenyl]-1-{10-[(4,4,5,5,5-pentafluoropentyl)thio]decyl}imidazolidine-2,4-dione The experimental protocol used is the same as that described for the synthesis of the compound of Example 1, 10-[(4,4,5,5,5-pentafluoropentypthio]decyl methanesulphonate (prepared according to an experimental protocol similar to that described in WO 2005077968) replacing 9-[(4,4,5,5,5-pentafluoropentyl)-thio]nonyl methanesulphonate. The expected compound is obtained in the form of a pale yellow oil with a yield of 13% (125 mg).

$^1$H NMR 400 MHz (DMSO-$d_6$) δ: 8.32 (d, 1H, Ph); 8.20 (d, 1H, Ph); 8.07 (dd, 1H, Ph); 3.29 (m, 2H, N$CH_2$); 2.57 (m, 2H, S$CH_2$); 2.47 (m, 2H, S$CH_2$); 2.27 (m, 2H, $CH_2$); 1.75 (m, 2H, $CH_2$); 1.61 (m, 2H, $CH_2$); 1.50 (m, 2H, $CH_2$); 1.46 (s, 6H, 2×$CH_3$); 1.29 (m, 12H, 6×$CH_2$).

Example 9

5,5-dimethyl-3-[4-nitro-3-(trifluoromethyl)phenyl]-1-{10-[(4,4,5,5,5-pentafluoropentyl)sulphinyl]decyl}imidazolidine-2,4-dione The experimental protocol used is the same as that described for the synthesis of the compound of Example 2, the compound of Example 8 replacing the compound of Example 1. The expected compound is obtained in the form of a pale yellow oil with a yield of 74% (71 mg).
$^1$H NMR 400 MHz (DMSO-d$_6$) δ: 8.32 (d, 1H, Ph); 8.20 (d, 1H, Ph); 8.07 (dd, 1H, Ph); 3.28 (m, 2H, NCH$_2$); 2.80 (m, 2H, S(=O)CH$_2$); 2.71 (m, 2H, S(=O)CH$_2$); 2.37 (m, 2H, CH$_2$); 1.92 (m, 2H, CH$_2$); 1.60 (m, 4H, 2×CH$_2$); 1.46 (s, 6H, 2×CH$_3$); 1.33 (m, 12H, 6×CH$_2$).

Example 10

5,5-dimethyl-3-[4-nitro-3-(trifluoromethyl)phenyl]-1-{11-[(4,4,5,5,5-pentafluoropentyl)thio]undecyl}imidazolidine-2,4-dione The experimental protocol used is the same as that described for the synthesis of the compound of Example 1, 10-[(4,4,5,5,5-pentafluoropentypthio]undecyl methanesulphonate (prepared according to an experimental protocol similar to that described in WO 2005077968) replacing 9-[(4,4,5,5,5-pentafluoropentyl)-thio]nonyl methanesulphonate. The expected compound is obtained in the form of a pale yellow oil with a yield of 43% (328 mg).
$^1$H NMR 400 MHz (DMSO-d$_6$) δ: 8.42 (d, 1H, Ph); 8.30 (d, 1H, Ph); 8.18 (dd, 1H, Ph); 3.38 (m, 2H, NCH$_2$); 2.67 (m, 2H, SCH$_2$); 2.57 (m, 2H, SCH$_2$); 2.37 (m, 2H, CH$_2$); 1.85 (m, 2H, CH$_2$); 1.71 (m, 2H, CH$_2$); 1.58 (m, 2H, CH$_2$); 1.56 (s, 6H, 2×CH$_3$); 1.40 (m, 14H, 7×CH$_2$).

Example 11

5,5-dimethyl-3-[4-nitro-3-(trifluoromethyl)phenyl]-1-{11-[(4,4,5,5,5-pentafluoropentyl)sulphinyl]undecyl}imidazolidine-2,4-dione The experimental protocol used is the same as that described for the synthesis of the compound of Example 2, Example 10 replacing the compound of Example 1. The expected compound is obtained in the form of a pale yellow oil with a yield of 72% (240 mg).
$^1$H NMR 400 MHz (DMSO-d$_6$) δ: 8.32 (d, 1H, Ph); 8.20 (d, 1H, Ph); 8.07 (dd, 1H, Ph); 3.28 (m, 2H, NCH$_2$); 2.75 (m, 4H, CH$_2$S(=O)CH$_2$); 2.40 (m, 2H, CH$_2$); 1.90 (m, 2H, CH$_2$); 1.60 (m, 4H, 2×CH$_2$); 1.46 (s, 6H, 2×CH$_3$); 1.39 (m, 2H, CH$_2$); 1.30 (m, 12H, 6×CH$_2$).

Example 12

5,5-dimethyl-3-[4-nitro-3-(trifluoromethyl)phenyl]-1-{9-[(4,4,4-trifluorobutyl)thio]nonyl}imidazolidine-2,4-dione 12.1) 1-(9-bromononyl)-5,5-dimethyl-3-[4-nitro-3-(trifluoromethyl)phenyl]-imidazolidine-2,4-dione The experimental protocol used is the same as that described for the synthesis of intermediate 4.1, 1,9-dibromononane replacing 1,5-diiodopentane. The expected compound is obtained in the form of a pale yellow oil with a yield of 45% (1.24 g).
$^1$H NMR 400 MHz (DMSO-d$_6$) δ: 8.32 (d, 1H, Ph); 8.20 (d, 1H, Ph); 8.07 (dd, 1H, Ph); 3.51 (m, 2H, CH$_2$Br); 3.29 (m, 2H, NCH$_2$); 1.78 (m, 2H, CH$_2$); 1.62 (m, 2H, CH$_2$); 1.46 (s, 6H, 2×CH$_3$); 1.32 (m, 10H, 5×CH$_2$).

12.2) 5,5-dimethyl-3-[4-nitro-3-(trifluoromethyl)phenyl]-1-{9-[(4,4,4-trifluorobutyl)thio]nonyl}imidazolidine-2,4-dione The experimental protocol used is the same as that described for the synthesis of Example 4, intermediate 12.1 replacing intermediate 4.1 and S-(4,4,4-trifluorobutyl)benzenecarbothioate (prepared according to WO 2005077968) replacing intermediate S-(4,4,5,5,5-pentafluoropentyl)benzene-carbothioate. The expected compound is obtained in the form of a pale yellow oil with a yield of 83% (231 mg).
$^1$H NMR 400 MHz (DMSO-d$_6$) δ: 8.42 (d, 1H, Ph); 8.30 (d, 1H, Ph); 8.18 (dd, 1H, Ph); 3.38 (m, 2H, NCH$_2$); 2.60 (m, 4H, CH$_2$SCH$_2$); 2.42 (m, 2H, CH$_2$); 1.82 (m, 2H, CH$_2$); 1.71 (m, 2H, CH$_2$); 1.61 (m, 2H, CH$_2$); 1.46 (s, 6H, 2×CH$_3$); 1.32 (m, 10H, 5×CH$_2$).

Example 13

5,5-dimethyl-3-[4-nitro-3-(trifluoromethyl)phenyl]-1-{9-[(4,4,4-trifluorobutyl)sulphinyl]nonyl}imidazolidine-2,4-dione The experimental protocol used is the same as that described for the synthesis of the compound of Example 2, the compound of Example 12 replacing the compound of Example 1. A pale yellow oil is obtained with a yield of 73% (140 mg).
$^1$H NMR 400 MHz (DMSO-d$_6$) δ: 8.32 (d, 1H, Ph); 8.20 (d, 1H, Ph); 8.08 (dd, 1H, Ph); 3.30 (m, 2H, NCH$_2$); 2.71 (m, 4H, CH$_2$S(=O)CH$_2$); 2.41 (m, 2H, CH$_2$); 1.86 (m, 2H, CH$_2$); 1.62 (m, 4H, 2×CH$_2$); 1.46 (s, 6H, 2×CH$_3$); 1.35 (m, 10H, 5×CH$_2$).

Example 14

5,5-dimethyl-3-[4-nitro-3-(trifluoromethyl)phenyl]-1-{9-[(3,3,4,4,5,5,6,6,6-nonafluorohexyl)thio]nonyl}imidazolidine-2,4-dione The experimental protocol used is the same as that described for the synthesis of Example 4, intermediate 12.1 replacing intermediate 4.1 and S-(3,3,4,4,5,5,6,6,6-nonafluorohexyl)benzenecarbothioate (prepared according to WO 2005077968) replacing intermediate S-(4,4,5,5,5-pentafluoropentyl)benzenecarbothioate. The expected compound is obtained in the form of a pale yellow oil with a yield of 78% (212 mg).
$^1$H NMR 400 MHz (DMSO-d$_6$) δ: 8.42 (d, 1H, Ph); 8.30 (d, 1H, Ph); 8.18 (dd, 1H, Ph); 3.39 (m, 2H, NCH$_2$); 2.80 (m, 2H, SCH$_2$); 2.64 (m, 2H, SCH$_2$); 2.59 (m, 2H, CH$_2$); 1.71 (m, 2H, CH$_2$); 1.61 (m, 2H, CH$_2$); 1.56 (s, 6H, 2×CH$_3$); 1.41 (m, 10H, 5×CH$_2$).

Example 15

5,5-dimethyl-3-[4-nitro-3-(trifluoromethyl)phenyl]-1-{9-[(3,3,4,4,5,5,6,6,6-nonafluorohexyl)sulphinyl]nonyl}imidazolidine-2,4-dione The experimental protocol used is the same as that described for the synthesis of the compound of Example 2, the compound of Example 14 replacing the compound of Example 1. A pale yellow oil is obtained with a yield of 85% (145 mg).
$^1$H NMR 400 MHz (DMSO-d$_6$) δ: 8.32 (d, 1H, Ph); 8.20 (d, 1H, Ph); 8.07 (dd, 1H, Ph); 3.29 (m, 2H, NCH$_2$); 3.00 (m, 2H, S(=O)CH$_2$); 2.78 (m, 2H, S(=O)CH$_2$); 2.65 (m, 2H, CH$_2$); 1.62 (m, 4H, 2×CH$_2$); 1.46 (s, 6H, 2×CH$_3$); 1.39 (m, 2H, CH$_2$); 1.31 (m, 8H, 4×CH$_2$).

Example 16

3-[4-amino-3-(trifluoromethyl)phenyl]-5,5-dimethyl-1-{9-[(4,4,5,5,5-pentafluoropentyl)thio]nonyl}imidazolidine-2,4-dione $SnCl_2$, $2H_2O$ (3.84 g, 17 mmoles) is added to the compound of Example 1 (1.08 g, 1.7 mmole) dissolved in AcOEt (30 ml). The reaction mixture is heated under reflux until the starting compound disappears (5 h 30) and then cooled down using an ice bath. After dilution with AcOEt (30 ml), the mixture is poured onto a 1M aqueous solution of $NaHCO_3$ (120 ml). The mixture is stirred for a few hours during which time a white precipitate forms. This precipitate is eliminated by filtration on celite. The filtrate is decanted and the organic solution is dried over $Na_2SO_4$, filtered and concentrated to dryness under vacuum. The expected compound is obtained in the form of a yellow oil with a yield of 84% (868 mg).

$^1$H NMR 400 MHz (DMSO-$d_6$) δ: 7.31 (d, 1H, Ph); 7.22 (dd, 1H, Ph); 6.86 (d, 1H, Ph); 5.80 (s, 2H, $NH_2$); 3.27 (m, 2H, $NCH_2$); 2.57 (m, 2H, $SCH_2$); 2.47 (m, 2H, $SCH_2$); 2.29 (m, 2H, $CH_2$); 1.74 (m, 2H, $CH_2$); 1.58 (m, 2H, $CH_2$); 1.48 (m, 2H, $CH_2$); 1.39 (s, 6H, 2×$CH_3$); 1.25 (m, 10H, 5×$CH_2$).

Example 17

N-[4-(4,4-dimethyl-2,5-dioxo-3-{9-[(4,4,5,5,5-pentafluoropentythio]-nonyl}imidazolidin-1-yl)-2-(trifluoromethyl)phenyl]acetamide Acetyl chloride (1 ml, 37 eq.) is added dropwise at 23° C. to a solution of Example 16 (230 mg, 0.38 mmole) in anhydrous $CH_2Cl_2$ (2 ml). The reaction mixture is stirred for 1 hour and concentrated to dryness under vacuum. The evaporation residue is purified on a silica column (eluent:. Heptane/AcOEt:1/1 to 3/7). After collection and concentration of the pure fractions, the expected compound is obtained in the form of a colourless oil which crystallizes slowly with a yield of 91% (225 mg). Melting point: 84-86° C.

$^1$H NMR 400 MHz (DMSO-$d_6$) δ: 9.67 (s, 1H, NH); 7.80 (d, 1H, Ph); 7.69 (dd, 1H, Ph); 7.58 (d, 1H, Ph); 3.28 (m, 2H, $NCH_2$); 2.57 (m, 2H, $SCH_2$); 2.48 (m, 2H, $SCH_2$); 2.30 (m, 2H, $CH_2$); 2.06 (s, 3H, $CH_3$—CO); 1.74 (m, 2H, $CH_2$); 1.60 (m, 2H, $CH_2$); 1.48 (m, 2H, $CH_2$); 1.43 (s, 6H, 2×$CH_3$); 1.28 (m, 10H, 5×$CH_2$).

Example 18

N-[4-(4,4-dimethyl-2,5-dioxo-3-{9-[(4,4,5,5,5-pentafluoropentyl)sulphinyl]-nonyl}imidazolidin-1-yl)-2-(trifluoromethyl)phenyl]acetamide The experimental protocol used is the same as that described for the synthesis of the compound of Example 2, the compound of Example 17 replacing the compound of Example 1. A colourless oil is obtained with a yield of 61% (98 mg).

$^1$H NMR 400 MHz (DMSO-$d_6$) δ: 9.63 (s, 1H, NH); 7.81 (d, 1H, Ph); 7.68 (dd, 1H, Ph); 7.58 (d, 1H, Ph); 3.28 (m, 2H, $NCH_2$); 2.72 (m, 4H, $CH_2S(=O)CH_2$); 2.38 (m, 2H, $CH_2$); 2.06 (s, 3H, $CH_3$—CO); 1.90 (m, 2H, $CH_2$); 1.60 (m, 4H, 2×$CH_2$); 1.44 (s, 6H, 2×$CH_3$); 1.39 (m, 2H, $CH_2$); 1.30 (m, 8H, 4×$CH_2$).

Example 19

4-(4,4-dimethyl-2,5-dioxo-3-{9-[(4,4,5,5,5-pentafluoropentylsulphanyl]nonyl}imidazolidin-1-yl)-2-(trifluoromethyl)benzonitrile

19.1) 4-(4,4-dimethyl-2,5-dioxoimidazolidin-1-yl)-2-(trifluoromethyl)benzonitrile A mixture of 4-fluoro-2-(trifluoromethyl)benzonitrile (5.67 mg, 30 mmoles), 5,5-dimethyl-hydantoin (7.68 g, 60 mmoles), $K_2CO_3$ (8.28 g, 60 mmoles) in DMF (45 ml) is distributed in equal parts into three tubes to be placed in a microwave oven. Under magnetic stirring, each tube is irradiated at 140° C. for 20 minutes. The reaction masses are then combined, poured into water (200 ml) and extracted with AcOEt (2×75 ml). The organic phases are combined, washed with salt water, dried over $Na_2SO_4$ and filtered. The filtrate is concentrated under reduced pressure and the residue crystallized from $Et_2O$ (25 ml). After recrystallization from EtOH (75 ml), the powder is filtered and dried under vacuum. The expected compound is obtained in the form of a white solid with a yield of 46% (4.1 g). Melting point: 212-213° C.

$^1$H NMR 400 MHz (DMSO-$d_6$) δ: 8.80 (s, 1H, NH); 8.29 (d, 1H, Ph); 8.18 (s, 1H, Ph); 8.02 (d, 1H, Ph); 1.42 (s, 6H, 2×$CH_3$).

19.2) 4-[3-(9-bromononyl)-4,4-dimethyl-2,5-dioxoimidazolidin-1-yl]-2-(trifluoromethyl)benzonitrile The experimental protocol used is the same as that described for the synthesis of intermediate 12.1, intermediate 19.1 replacing 5,5-dimethyl-3-[4-nitro-3-(trifluoromethyl)phenyl]imidazolidine-2,4-dione. The expected compound is obtained in the form of a yellow oil with a yield of 80%.

$^1$H NMR 400 MHz (DMSO-$d_6$) δ: 8.29 (d, 1H, Ph); 8.18 (d, 1H, Ph); 8.04 (dd, 1H, Ph); 3.50 (m, 2H, $CH_2Br$); 3.29 (m, 2H, $NCH_2$); 1.78 (m, 2H, $CH_2$); 1.61 (m, 2H, $CH_2$); 1.46 (s, 6H, 2×$CH_3$); 1.32 (m, 10H, 5×$CH_2$).

19.3) 4-(4,4-dimethyl-2,5-dioxo-3-{9-[(4,4,5,5,5-pentafluoropentylsulphanyl]nonyl}imidazolidin-1-yl)-2-(trifluoromethyl)benzonitrile The experimental protocol used is the same as that described for the synthesis of intermediate 4.2, intermediate 19.2 replacing intermediate 4.1. The expected compound is obtained in the form of a yellow oil with a yield of 89%.

$^1$H NMR 400 MHz (DMSO-$d_6$) δ: 8.24 (d, 1H, Ph); 8.13 (d, 1H, Ph); 7.99 (dd, 1H, Ph); 3.22 (m, 2H, $NCH_2$); 2.52 (m, 2H, $SCH_2$); 2.44 (m, 2H, $SCH_2$); 2.26 (m, 2H, $CH_2$); 1.70 (m, 2H, $CH_2$); 1.56 (m, 2H, $CH_2$); 1.48 (m, 2H, $CH_2$); 1.40 (s, 6H, 2×$CH_3$); 1.21 (m, 10H, 5×$CH_2$).

Example 20

4-(4,4-dimethyl-2,5-dioxo-3-{9-[(4,4,5,5,5-pentafluoropentyl)sulphinyl]nonyl}imidazolidin-1-yl)-2-(trifluoromethyl)benzonitrile The experimental protocol used is the same as that described for the synthesis of the compound of Example 2, the compound of Example 19 replacing the compound of Example 1. A colourless oil is obtained with a yield of 78%.

$^1$H NMR 400 MHz (DMSO-$d_6$) δ: 8.29 (d, 1H, Ph); 8.18 (d, 1H, Ph); 8.03 (dd, 1H, Ph); 3.28 (m, 2H, $NCH_2$); 2.82 (m, 4H,

CH$_2$S(=O)CH$_2$); 2.38 (m, 2H, CH$_2$); 1.89 (m, 2H, CH$_2$); 1.62 (m, 4H, 2×CH$_2$); 1.45 (s, 6H, 2×CH$_3$); 1.31 (m, 10H, 5×CH$_2$).

Example 21

4-(4,4-dimethyl-2,5-dioxo-3-{9-[(4,4,5,5,5-pentafluoropentyl)sulphanyl]nonyl}imidazolidin-1-yl)-2-(trifluoromethyl)benzamide The compound of Example 19 (359 mg, 0.58 mmole) is mixed with trifluoroacetic acid (4 ml) and sulphuric acid (1 ml). After stirring for 15 hours at 60° C., the reaction medium is poured onto a water-ice mixture and extracted with AcOEt (2×50 ml). The organic phases are combined and washed successively with water, a saturated aqueous solution of NaHCO$_3$ and salt water. The organic solution is then dried over Na$_2$SO$_4$, filtered and the solvent evaporated off under reduced pressure. The evaporation residue is purified by chromatography on a silica column (eluent: Heptane/AcOEt:9/1 to 4/6). The expected compound is obtained in the form of a yellow oil with a yield of 70%.

LC-MS (UV): purity (220 nM): 99%. ES$^-$: (M+TFA-H)$^-$: 746.

Example 22

4-(4,4-dimethyl-2,5-dioxo-3-{9-[(4,4,5,5,5-pentafluoropentyl)sulphinyl]nonyl}imidazolidin-1-yl)-2-(trifluoromethyl)benzamide The experimental protocol used is the same as that described for the synthesis of the compound of Example 2, the compound of Example 21 replacing the compound of Example 1. A colourless oil is obtained with a yield of 50%.

$^1$H NMR 400 MHz (DMSO-d$_6$) δ: 7.96 (broad s, 1H, ½ NH$_2$); 7.81 (s, 1H, Ph); 7.70 (d, 1H, Ph); 7.59 (m, 2H, Ph+½ NH$_2$); 3.25 (m, 2H, NCH$_2$); 2.70 (m, 4H, CH$_2$S(=O)CH$_2$); 2.30 (m, 2H, CH$_2$); 1.83 (m, 2H, CH$_2$); 1.57 (m, 4H, 2×CH$_2$); 1.40 (s, 6H, 2×CH$_3$); 1.25 (m, 10H, 5×CH$_2$).

Example 23

5,5-dimethyl-3-(3-methyl-4-nitrophenyl)-1-{9-[(4,4,5,5,5-pentafluoro pentyl)sulphanyl]nonyl}imidazolidine-2,4-dione 23.1) 5,5-dimethyl-3-(3-methyl-4-nitrophenyl)imidazolidine-2,4-dione A mixture of 5-fluoro-2-nitrotoluene (1.55 g, 10 mmoles), 5,5-dimethylhydantoin (1.28 g, 10 mmoles), K$_2$CO$_3$ (1.38 g, 10 mmoles) in DMF (15 ml) is introduced into a vial intended to be placed in a microwave oven and irradiated at 100° C. for 70 minutes, under magnetic stirring. The reaction mixture is then poured into water (200 ml) and extracted with AcOEt (2×75 ml). The organic phases are combined, washed with salt water, dried over Na$_2$SO$_4$ and filtered. The filtrate is concentrated under reduced pressure and the residue is purified by chromatography on a silica column (eluent: Heptane/AcOEt:7/3). The expected compound is obtained in the form of a white solid with a yield of 25% (666 mg). Melting point: 177-178° C.

$^1$H NMR 400 MHz (DMSO-d$_6$) δ: 8.70 (s, 1H, NH); 8.10 (d, 1H, Ph); 7.58 (s, 1H, Ph); 7.52 (dd, 1H, Ph); 2.54 (s, 3H, CH$_3$); 1.41 (s, 6H, 2×CH$_3$).

23.2) 1-(9-bromononyl)-5,5-dimethyl-3-(3-methyl-4-nitrophenyl)imidazolidine-2,4-dione The experimental protocol used is the same as that described for the synthesis of intermediate 12.1, intermediate 23.1 replacing 5,5-dimethyl-3-[4-nitro-3-(trifluoromethyl)phenyl]imidazolidine-2,4-dione. The expected compound is obtained in the form of a yellow oil with a yield of 74%.

$^1$H NMR 400 MHz (DMSO-d$_6$) δ: 8.10 (d, 1H, Ph); 7.59 (d, 1H, Ph); 7.53 (dd, 1H, Ph); 3.51 (m, 2H, CH$_2$Br); 3.29 (m, 2H, NCH$_2$); 2.54 (s, 3H, 1 CH$_3$); 1.78 (m, 2H, CH$_2$); 1.61 (m, 2H, CH$_2$); 1.44 (s, 6H, 2×CH$_3$); 1.32 (m, 10H, 5×CH$_2$).

23.3) 5,5-dimethyl-3-(3-methyl-4-nitrophenyl)-1-{9-[(4,4,5,5,5-pentafluoropentyl) sulphanyl]nonyl}imidazolidine-2,4-dione The experimental protocol used is the same as that described for the synthesis of intermediate 4.2, intermediate 23.2 replacing intermediate 4.1. The expected compound is obtained in the form of a yellow oil with a yield of 90%.

$^1$H NMR 400 MHz (DMSO-d$_6$) δ: 8.10 (d, 1H, Ph); 7.59 (d, 1H, Ph); 7.54 (dd, 1H, Ph); 3.26 (m, 2H, NCH$_2$); 2.56 (m, 5H, SCH$_2$+CH$_3$); 2.49 (m, 2H, SCH$_2$); 2.28 (m, 2H, CH$_2$); 1.74 (m, 2H, CH$_2$); 1.61 (m, 2H, CH$_2$); 1.52 (m, 2H, CH$_2$); 1.45 (s, 6H, 2×CH$_3$); 1.28 (m, 10H, 5×CH$_2$).

Example 24

5,5-dimethyl-3-(3-methyl-4-nitrophenyl)-1-{9-[(4,4,5,5,5-pentafluoro pentyl)sulphinyl]nonyl}imidazolidine-2,4-dione The experimental protocol used is the same as that described for the synthesis of the compound of Example 2, the compound of Example 23 replacing the compound of Example 1. A colourless oil is obtained with a yield of 50%.

$^1$H NMR 400 MHz (DMSO-d$_6$) δ: 8.05 (s, 1H, Ph); 7.53 (d, 1H, Ph); 7.49 (m, 1H, Ph); 3.24 (m, 2H, NCH$_2$); 2.70 (m, 4H, CH$_2$S(=O)CH$_2$); 2.49 (s, 3H, CH$_3$); 2.30 (m, 2H, CH$_2$); 1.85 (m, 2H, CH$_2$); 1.57 (m, 4H, 2×CH$_2$); 1.40 (s, 6H, 2×CH$_3$); 1.25 (m, 10H, 5×CH$_2$).

Example 25

3-(4-amino-3-methylphenyl)-5,5-dimethyl-1-{9-[(4,4,5,5,5-pentafluoro pentyl)sulphanyl]nonyl}imidazolidine-2,4-dione The experimental protocol is the same as that described for the compound of Example 16, the compound of Example 23 replacing the compound of Example 1. The expected compound is obtained in the form of a brown oil with a yield of 93%.

$^1$H NMR 400 MHz (DMSO-d$_6$) δ: 6.81 (d, 1H, Ph); 6.78 (dd, 1H, Ph); 6.60 (d, 1H, Ph); 5.02 (s, 2H, NH$_2$); 3.25 (m, 2H, NCH$_2$); 2.57 (m, 2H, SCH$_2$); 2.48 (m, 2H, SCH$_2$); 2.30 (m, 2H, CH$_2$); 2.04 (s, 3H, CH$_3$); 1.75 (m, 2H, CH$_2$); 1.55 (m, 2H, CH$_2$); 1.48 (m, 2H, CH$_2$); 1.37 (s, 6H, 2×CH$_3$); 1.22 (m, 10H, 5×CH$_2$).

Example 26

3-(4-amino-3-methylphenyl)-5,5-dimethyl-1-{9-[(4,4,5,5,5-pentafluoro pentyl)sulphinyl]nonyl}imidazolidine-2,4-dione The experimental protocol used is the same as that described for the synthesis of the compound of Example 2, the compound of Example 25 replacing the compound of Example 1. A colourless oil is obtained with a yield of 56%.

$^1$H NMR 400 MHz (DMSO-d$_6$) δ: 6.82 (d, 1H, Ph); 6.79 (dd, 1H, Ph); 6.60 (d, 1H, Ph); 5.02 (s, 2H, NH$_2$); 3.25 (m, 2H, NCH$_2$); 2.72 (m, 4H, CH$_2$S(=O)CH$_2$); 2.34 (m, 2H, CH$_2$); 2.04 (s, 3H, CH$_3$); 1.91 (m, 2H, CH$_2$); 1.61 (m, 4H, 2×CH$_2$); 1.41 (m, 8H, 2×CH$_3$+CH$_2$); 1.25 (m, 8H, 4×CH$_2$).

Example 27

1-[4-(4,4-dimethyl-2,5-dioxo-3-{9-[(4,4,5,5,5-pentafluoropentyl)sulphanyl]nonyl}imidazolidin-1-yl)-2-methylphenyl]-3-(1-methylpropyl)urea The compound of Example 25 (395 mg, 0.72 mmole) is dissolved in anhydrous 1,2-dichloroethane (10 ml) under an argon atmosphere, before the dropwise addition of sec-butylisocyanate (0.35 ml, 3 mmoles) at 23° C. The mixture is then heated under reflux for 24 hours. The reaction medium is then poured onto cold water and extracted using CH$_2$Cl$_2$. After decantation, the organic phase is washed with water and salt water. The organic solution is then dried over MgSO$_4$, filtered, concentrated to dryness under vacuum and the evaporation residue is purified on a silica column (eluent: heptane/AcOEt: 1/0 to 4/6). The expected compound is obtained in the form of a colourless oil with a yield of 36%.

$^1$H NMR 400 MHz (DMSO-d$_6$) δ: 7.96 (d, 1H, NH); 7.61 (s, 1H, NH); 7.07 (d, 1H, Ph); 7.02 (dd, 1H, Ph); 6.48 (d, 1H, Ph); 3.59 (m, 1H, CH); 3.26 (m, 2H, NCH$_2$); 2.57 (m, 2H, SCH$_2$); 2.48 (m, 2H, SCH$_2$); 2.28 (m, 2H, CH$_2$); 2.18 (s, 3H, CH$_3$); 1.74 (m, 2H, CH$_2$); 1.58-1.42 (m, 6H, 3×CH$_2$); 1.40 (s, 6H, 2×CH$_3$); 1.30 (m, 10H, 5×CH$_2$); 1.07 (d, 3H, CH$_3$); 0.88 (t, 3H, CH$_3$).

Example 28

1-[4-(4,4-dimethyl-2,5-dioxo-3-{9-[(4,4,5,5,5-pentafluoropentyl)sulphinyl]nonyl}imidazolidin-1-yl)-2-methylphenyl]-3-(1-methylpropyl)urea The experimental protocol used is the same as that described for the synthesis of the compound of Example 2, the compound of Example 25 replacing the compound of Example 1. A colourless oil is obtained with a yield of 63%.

$^1$H NMR 400 MHz (DMSO-d$_6$) δ: 7.96 (d, 1H, NH); 7.61 (s, 1H, NH); 7.07 (d, 1H, Ph); 7.02 (dd, 1H, Ph); 6.48 (d, 1H, Ph); 3.59 (m, 1H, CH); 3.26 (m, 2H, NCH$_2$); 2.86-2.65 (m, 4H, CH$_2$S(=O)CH$_2$); 2.40 (m, 2H, CH$_2$); 2.18 (s, 3H, CH$_3$); 1.91 (m, 2H, CH$_2$); 1.61 (m, 4H, 2×CH$_2$); 1.41 (m, 10H, 2×CH$_2$+2×CH$_3$); 1.30 (m, 8H, 4×CH$_2$); 1.07 (d, 3H, CH$_3$); 0.88 (t, 3H, CH$_3$).

Example 29 tert-butyl {[4-(4,4-dimethyl-2,5-dioxo-3-{9-[(4,4,5,5,5-pentafluoropentyl)sulphanyl]nonyl}imidazolidin-1-yl)-2-methylphenyl]sulphamoyl}carbamate A solution of the compound of Example 25 (612 mg, 1.1 mmole) and Et$_3$N (0.19 ml, 1.33 mmole) in anhydrous CH$_2$Cl$_2$ (30 ml) is stirred at 0° C. Then a solution of chlorosulphonyl isocyanate (0.11 ml, 1.22 mmole) in anhydrous CH$_2$Cl$_2$ (10 ml), cooled down to 0° C., is completed with t-BuOH (0.12 ml, 1.22 mmole) before being added rapidly to the solution of the compound of Example 25. The mixture is stirred for 30 min at 0° C. followed by 1 hour and a half at 23° C. The reaction medium is then washed successively with water (2×100 ml), a saturated aqueous solution of NaHCO$_3$ (50 ml) and salt water (50 ml). The organic solution is dried over Na$_2$SO$_4$, filtered and concentrated to dryness. The evaporation residue is purified on a silica column (eluent: Heptane/AcOEt: 1/0 to 6/4). The expected compound is obtained in the form of a white solid with a yield of 85%. Melting point 122-124° C.

$^1$H NMR 400 MHz (DMSO-d$_6$) δ: 11.07 (s, 1H, NH); 9.64 (s, 1H, NH); 7.28 (d, 1H, Ph); 7.20 (m, 2H, Ph); 3.28 (m, 21-1, NCH$_2$); 2.56 (m, 2H, SCH$_2$); 2.48 (m, 2H, SCH$_2$); 2.29 (m, 5H, CH$_2$+CH$_3$); 1.75 (m, 2H, CH$_2$); 1.58 (m, 2H, CH$_2$); 1.49 (m, 2H, CH$_2$); 1.42 (s, 15H, 2×CH$_3$+tBu); 1.28 (m, 10H, 5×CH$_2$).

Example 30

N-[4-(4,4-dimethyl-2,5-dioxo-3-{9-[(4,4,5,5,5-pentafluoropentyl)sulphanyl]nonyl}imidazolidin-1-yl)-2-methylphenyl]sulphamide A solution of HCl in ethyl ether (2N, 3 ml) is added in 31-ml portions to a solution of Example 29 (250 mg, 0.36 mmole) in a CH$_2$Cl$_2$/AcOEt mixture (5 ml/3 ml) cooled down to 0° C., and the mixture is stirred for 60 hours at 23° C. The volatiles are evaporated off under vacuum and the residue is taken up in a CH$_2$Cl$_2$ (50 ml) and NaHCO$_3$ (50 ml) mixture. After stirring and decantation, the organic phase is washed with water (50 ml) followed by salt water. After drying over Na$_2$SO$_4$, filtration and concentration to dryness, the residue is purified on a silica column (Heptane/AcOEt:10/0 to 1/1). The expected product is obtained in the form of a white solid with a yield of 76%. Melting point: 102-104° C.

$^1$H NMR 400 MHz (DMSO-d$_6$) δ: 8.60 (s, 1H, NH); 7.42 (d, 1H, Ph); 7.14 (m, 2H, Ph); 6.97 (s, 2H, NH$_2$); 3.26 (m, 2H, NCH$_2$); 2.57 (m, 2H, SCH$_2$); 2.48 (m, 2H, SCH$_2$); 2.27 (m, 5H, CH$_2$+CH$_3$); 1.75 (m, 2H, CH$_2$); 1.58 (m, 2H, CH$_2$); 1.52 (m, 2H, CH$_2$); 1.48 (m, 2H, CH$_2$); 1.41 (s, 6H, 2×CH$_3$); 1.30 (m, 10H, 5×CH$_2$).

Example 31

N-[4-(4,4-dimethyl-2,5-dioxo-3-{9-[(4,4,5,5,5-pentafluoropentyl)sulphinyl]nonyl}imidazolidin-1-yl)-2-methylphenyl]sulphamide The experimental protocol used is the same as that described for the synthesis of the compound of Example 2, the compound of Example 30 replacing the compound of Example 1. A white solid is obtained with a yield of 62%.

$^1$H NMR 400 MHz (DMSO-d$_6$) δ: 8.60 (s, 1H, NH); 7.42 (d, 1H, Ph); 7.14 (m, 2H, Ph); 6.97 (s, 2H, NH$_2$); 3.28 (m, 2H, NCH$_2$); 2.78 (m, 4H, CH$_2$S(=O)CH$_2$); 2.38 (m, 2H, CH$_2$); 2.29 (s, 3H, CH$_3$); 1.90 (m, 2H, CH$_2$); 1.60 (m, 4H, 2×CH$_2$); 1.40 (m, 8H, 2×CH$_3$+CH$_2$); 1.30 (m, 8H, 4×CH$_2$).

Example 32

N-[4-(4,4-dimethyl-2,5-dioxo-3-{9-[(4,4,5,5,5-pentafluoropentyl)sulphonyl]nonyl}imidazolidin-1-yl)-2-methylphenyl]sulphamide The experimental protocol used is the same as that described for the synthesis of the compound of Example 3, the compound of Example 31 replacing the compound of Example 2. A colourless oil is obtained.

¹H NMR 400 MHz (DMSO-d₆) δ: 8.55 (s, 1H, NH); 7.37 (d, 1H, Ph); 7.09 (m, 2H, Ph); 6.92 (s, 2H, NH₂); 3.15 (m, 4H, CH₂S(=O)₂CH₂); 3.05 (m, 2H, NCH₂); 2.32 (m, 2H, CH₂); 2.24 (s, 3H, CH₃); 1.91 (m, 2H, CH₂); 1.60 (m, 4H, 2×CH₂); 1.39 (m, 8H, 2×CH₃+CH₂); 1.22 (m, 8H, 4×CH₂).

Example 33

3-[4-amino-3-(trifluoromethyl)phenyl]-5,5-dimethyl-1-{9-[(4,4,5,5-pentafluoropentyl)sulphinyl]nonyl}imidazolidine-2,4-dione The experimental protocol used is the same as that described for the synthesis of the compound of Example 3, the compound of Example 16 replacing the compound of Example 2.

¹H NMR 400 MHz (DMSO-d₆) δ: 7.30 (d, 1H, Ph); 7.21 (dd, 1H, Ph); 6.85 (d, 1H, Ph); 5.80 (s, 1H, NH); 3.27 (m, 2H, NCH₂); 2.74 (m, 41-1, CH₂S(=O)CH₂); 2.38 (m, 2H, CH₂); 1.90 (m, H, CH₂); 1.60 (m, 4H, 2×CH₂); 1.40 (s, 8H, 2×CH₃+CH₂); 1.29 (m, 8H, 4×CH₂).

Example 34

7-[4-nitro-3-(trifluoromethyl)phenyl]-5-{9-[(4,4,5,5,5-pentafluoropentyl)sulphinyl]nonyl}-5,7-diazaspiro[3.4]octane-6,8-dione 34.1) 5,7-diazaspiro[3.4]octane-6,8-dione Sodium cyanide (1.47 g, 30 mmole) then ammonium carbonate (7.5 g, 78 mmole) are added under argon and at 23° to a solution of cyclobutanone (1.49 ml, 20 mmole) diluted in an ethanol-water solvent mixture (16 ml). The reaction mixture is heated for 6 hours at 70° C. After cooling down the reaction medium, water (15 ml) is poured in, then a solution of concentrated hydrochloric acid (13 ml) is added carefully. After stirring for 10 hours at 23° C. the ethanol and part of the water content of the reaction mixture are evaporated with a rotary evaporator. The precipitate is filtered on frit then washed with water. The expected compound is obtained in the form of a beige powder with a yield of 39% (1.1 g).

¹H NMR 400 MHz (DMSO-d₆) δ: 10.49 (se, 1H, NH); 8.27 (s, 1H, NH); 2.31-2.37 (m, 2H, CH₂); 2.19-2.27 (m, 2H, CH₂); 1.83-1.90 (m, 1H, CH$_A$); 1.71-1.76 (m, 1H, CH$_B$).

Melting point: 223-225° C.

34.2) 7-[4-nitro-3-(trifluoromethyl)phenyl]-5,7-diazaspiro[3.4]octane-6,8-dione

Potassium carbonate (1.09 g, 7.85 mmole) and the compound 5-fluoro-2-nitro-3-(trifluoromethyl)phenyl]-imidazolidine-2,4-dione (500 mg, 1.6 mmole) are added under argon to a solution of 5,7-diazaspiro[3.4]octane-6,8-dione (prepared previously) (221 mg, 0.74 mmole) in DMF (6 ml). The reaction mixture is heated at 65° C. for 2 hours then stirring is maintained for 12 hours at 23° C. The reaction medium is poured into a saturated aqueous solution of NH₄Cl (25 ml) and extracted with AcOEt (2×25 ml). The organic phases are combined and washed successively with water (25 ml) and salt water (25 ml). After drying over Na₂SO₄, the organic solution is filtered and concentrated under vacuum. The evaporation residue is purified on a silica column (eluent: Heptane/AcOEt:7/3 to 3/7). After washing with isopentane then filtration, the expected compound is obtained in the form of a pale yellow powder with a yield of 50% (645 mg).

¹H NMR 400 MHz (DMSO-d₆) δ: 9.15 (s, 1H, NH); 8.30 (d, 1H, Ph); 8.18 (d, 1H, Ph); 8.00 (dd, 1H, Ph); 2.51 (m, 2H, CH₂); 2.37 (m, 2H, CH₂); 1.94 (m, 1H, CH$_A$); 1.73 (m, 1H, CH$_B$).

34.3) 7-[4-nitro-3-(trifluoromethyl)phenyl]-5-{9-[(4,4,5,5,5-pentafluoropentyl)sulphanyl]nonyl}-5,7-diazaspiro[3.4]octane-6,8-dione NaH (to 60%) (44 mg, 1.1 mmole) is added under argon to a solution of 7-[4-nitro-3-(trifluoromethyl)phenyl]-5,7-diazaspiro[3.4]octane-6,8-dione (329 mg, 1 mmole) in anhydrous DMF (9 ml). A release of gas accompanies the change in colour of the reaction medium which becomes orange. Stirring is maintained for 1 hour at 23° C. before adding 9-[(4,4,5,5,5-pentafluoropentyl)-thio]nonyl methanesulphonate (prepared according to an experimental protocol described in WO 2005077968) (332 mg, 0.8 mmole). After reaction for 15 hours, the reaction medium is poured into water (25 ml) and extracted with AcOEt (2×25 ml). The organic phases are combined and washed successively with water (25 ml) and salt water (25 ml). After drying over Na₂SO₄, the organic solution is filtered and concentrated under vacuum. The evaporation residue is purified on an RP18 silica column (eluent: ACN/H₂O: 8/2 to 100). The expected compound is obtained in the form of a colourless oil with a yield of 33% (214 mg).

¹H NMR 400 MHz (DMSO-d₆) δ: 8.31 (d, 1H, Ph); 8.18 (d, 1H, Ph); 8.05 (dd, 1H, Ph); 3.40 (m, 2H, NCH₂); 2.55 (m, 4H, SCH₂, CH₂); 2.45 (m, 2H, SCH₂); 2, 30 (m, 2H, CH₂), 2.03 (m, 1H, CH$_A$); 1.81 (m, 2H, CH₂); 1.74 (m, 3H, CH₂, CH$_B$); 1.62 (m, 2H, CH₂); 1.49 (s, 2H, CH₂); 1.30 (m, 10H, 5×CH₂).

34.4) 7-[4-nitro-3-(trifluoromethyl)phenyl]-5-{9-[(4,4,5,5,5-pentafluoropentyl)sulphinyl]nonyl}-5,7-diazaspiro[3.4]octane-6,8-dione Compound 34.4 described below was synthesized according to a method similar to that described in Example 2, intermediate 34.3 replacing 5,5-dimethyl-3-[4-nitro-3-(trifluoromethyl)phenyl]-1-{9-[(4,4,5,5,5-pentafluoropentyl)thio]nonyl}imidazolidine-2,4-dione of Example 1. The expected compound is obtained in the form of a pale yellow oil with a yield of 79% (170 mg).

¹H NMR 400 MHz (DMSO-d₆) δ: 8.31 (d, 1H, Ph); 8.18 (d, 1H, Ph); 8.06 (dd, 1H, Ph); 3.44 (m, 2H, NCH₂); 2.61 (m, 6H, CH₂S(=O)CH₂, CH₂); 2.43 (m, 4H, 2CH₂); 2.03 (m, 1H, CH$_A$); 1.87 (m, 3H, CH₂, CH$_B$); 1.62 (m, 4H, 2CH₂); 1.31 (m, 10H, 5×CH₂).

Example 35

5,5-dimethyl-3-[4-nitro-2-(trifluoromethyl)phenyl]-1-{9-[(4,4,5,5,5-pentafluoropentyl)sulphinyl]nonyl}imidazolidine-2,4-dione 35.1) 5,5-dimethyl-3-[4-nitro-2-(trifluoromethyl)phenyl]imidazolidine-2,4-dione The experimental protocol used is the same as that described for the synthesis of the compound of Example 19.1, 1-fluoro-4-nitro-2-(trifluoromethyl)benzene replacing 4-fluoro-2-(trifluoromethyl)benzonitrile. The expected compound is obtained in the form of a white powder with a yield of 77%.

Melting point: 201-203° C.

¹H NMR 400 MHz (DMSO-d₆) δ: 8.76 (s, 1H, NH); 8.67 (dd, 1H, Ph); 8.58 (d, 1H, Ph); 8.04 (d, 1H, Ph); 1.44 (s, 3H, CH₃); 1.38 (s, 3H, CH₃).

35.2) 5,5-dimethyl-3-[4-nitro-2-(trifluoromethyl) phenyl]-1-{9-[(4,4,5,5,5-pentafluoropentyl)sulphanyl]nonyl}imidazolidine-2,4-dione The experimental protocol used is the same as that described for the synthesis of Example 1, intermediate 35.1 replacing 5,5-dimethyl-3-[4-nitro-3-(trifluoromethyl)phenyl]imidazolidine-2,4-dione. The expected compound is obtained in the form of a colourless oil with a yield of 50%.

¹H NMR 400 MHz (DMSO-d₆) δ: 8.69 (dd, 1H, Ph); 8.57 (d, 1H, Ph); 8.05 (d, 1H, Ph); 3.27 (m, 2H, NCH₂); 2.57 (m, 2H, SCH₂); 2.48 (m, 2H, SCH₂); 2.29 (m, 2H, CH₂); 1.76 (m, 2H, CH₂); 1.59 (m, 2H, CH₂); 1.40 (s, 8H, 2×CH₃+CH₂); 1.28 (m, 10H, 5×CH₂).

35.3) 5,5-dimethyl-3-[4-nitro-2-(trifluoromethyl) phenyl]-1-{9-[(4,4,5,5,5-pentafluoropentyl)sulphinyl]nonyl}imidazolidine-2,4-dione The experimental protocol used is the same as that described for the synthesis of the compound of Example 2, intermediate 35.2 replacing 5,5-dimethyl-3-[4-nitro-3-(trifluoromethyl)phenyl]-1-{9-[(4,4,5,5,5-pentafluoropentyl)thio]nonyl}imidazolidine-2,4-dione of Example 1. The expected compound is obtained in the form of a colourless oil with a yield of 85%.

¹H NMR 400 MHz (DMSO-d₆) δ: 8.69 (dd, 1H, Ph); 8.57 (d, 1H, Ph); 8.05 (d, 1H, Ph); 3.30 (m, 2H, NCH₂); 2.82 (m, 2H, S(=O)CH₂); 2.66 (m, 2H, S(=O)CH₂); 2.39 (m, 2H, CH₂); 1.90 (m, 2H, CH₂); 1.60 (m, 4H, 2CH₂); 1.50 (s, 3H, CH₃); 1.41 (s, 3H, CH₃); 1.30 (m, 10H, 5×CH₂).

Example 36

5,5-dimethyl-3-[4-nitro-3-(trifluoromethyl)phenyl]-1-[2-(2-{2-[(4,4,5,5,5-pentafluoropentyl)sulphanyl]ethoxy}ethoxy)ethyl]imidazolidine-2,4-dione 36.1) 1-{2-[2-(2-iodoethoxy)ethoxy]ethyl}-5,5-dimethyl-3-[4-nitro-3-(trifluoromethyl)phenyl]imidazolidine-2,4-dione The experimental protocol used is the same as that described for the synthesis of intermediate 4.1, 1,2bis-(2-iodoethoxy)ethane replacing 1,5-diiodopentane. The expected compound is obtained in the form of a pale yellow oil with a yield of 59% (666 mg).

¹H NMR 400 MHz (DMSO-d₆) δ: 8.32 (d, 1H, Ph); 8.20 (d, 1H, Ph); 8.08 (m, 1H, Ph); 3.64 (m, 4H, 2×OCH₂); 3.57 (s, 4H, 2×OCH₂); 3.51 (m, 2H, NCH₂); 3.29 (m, 2H, CH₂I); 1.47 (s, 6H, 2×CH₃).

36.2) 5,5-dimethyl-3-[4-nitro-3-(trifluoromethyl)phenyl]-1-[2-(2-{2-[(4,4,5,5,5-pentafluoropentyl)sulphanyl]ethoxy}ethoxy)ethyl]imidazolidine-2,4-dione The experimental protocol used is the same as that described for the synthesis of Example 4, intermediate 36.1 replacing 1-(5-iodopentyl)-5,5-dimethyl-3-[4-nitro-3-(trifluoromethyl)phenyl]imidazolidine-2,4-dione. The expected compound is obtained in the form of a colourless oil with a yield of 73%.

¹H NMR 400 MHz (DMSO-d₆) δ: 8.32 (d, 1H, Ph); 8.20 (d, 1H, Ph); 8.08 (m, 1H, Ph); 3.52 (m, 10H, 5×CH₂); 2.63 (s, 4H, 2×CH₂); 2.28 (m, 2H, CH₂); 1.75 (m, 2H, CH₂); 1.47 (s, 6H, 2×CH₃).

Example 37

5,5-dimethyl-3-[4-nitro-3-(trifluoromethyl)phenyl]-1-[2-(2-{2-[(4,4,5,5,5-pentafluoropentyl)sulphinyl]ethoxy}ethoxy)ethyl]imidazolidine-2,4-dione Compound 37 described below was synthesized according to a method similar to that described in Example 2 using compound 36 as starting reagent replacing 5,5-dimethyl-3-[4-nitro-3-(trifluoromethyl)phenyl]-1-{9-[(4,4,5,5,5-pentafluoropentyl)thio]nonyl}imidazolidine-2,4-dione. The expected compound is obtained in the form of a pale yellow oil with a yield of 88%.

¹H NMR 400 MHz (DMSO-d₆) δ: 8.32 (d, 1H, Ph); 8.20 (d, 1H, Ph); 8.07 (m, 1H, Ph); 3.76 (m, 2H, CH₂); 3.55 (m, 8H, 8×CH₂); 3.00 (m, 1H, CH); 2.85 (m, 3H, 2×CH₂+CH); 2.35 (m, 2H, CH₂); 1.89 (m, 2H, CH₂); 1.48 (s, 6H, 2CH₃).

Example 38

N-[4-{4,4-dimethyl-2,5-dioxo-3-[2-(2-{2-[(4,4,5,5,5-pentafluoropentyl)sulphanyl]ethoxy}ethoxy)ethyl]imidazolidin-1-yl}-2-(trifluoromethyl)phenyl]acetamide 38.1) 3-[4-amino-3-(trifluoromethyl)phenyl]-5,5-dimethyl-1-[2-(2-{2-[(4,4,5,5,5-pentafluoropentyl)sulphanyl]ethoxy}ethoxy)ethyl]imidazolidine-2,4-dione Compound 38 described below was synthesized according to a method similar to that described in Example 16 using compound 36 as starting reagent replacing 5,5-dimethyl-3-[4-nitro-3-(trifluoromethyl)phenyl]-1-{9-[(4,4,5,5,5-pentafluoropentypthio]nonyl}imidazolidine-2,4-dione. The expected compound is obtained in the form of a pale yellow oil with a yield of 88%.

MH+ experimental=596.1; M theoretical=595.2

38.2) N-[4-{4,4-dimethyl-2,5-dioxo-3-[2-(2-{2-[(4,4,5,5,5-pentafluoropentyl)sulphanyl]ethoxy}ethoxy)ethyl]imidazolidin-1-yl}-2-(trifluoromethyl)phenyl]acetamide Compound 38 described below was synthesized according to a similar method to that described in Example 17 using compound 38.1 as starting reagent replacing 3-[4-amino-3-(trifluoromethyl)phenyl]-5,5-dimethyl-1-{9-[(4,4,5,5,5-pentafluoropentypthio]nonyl}imidazolidine-2,4-dione. The expected compound is obtained in the form of a pale yellow oil with a yield of 88%.

¹H NMR 400 MHz (DMSO-d₆) δ: 9.64 (s, 1H, Ph); 7.80 (d, 1H, Ph); 7.68 (m, 1H, Ph); 7.59 (m, 1H, Ph); 3.52 (m, 10H, 5×CH₂); 2.63 (m, 4H, 2×CH₂); 2.35 (m, 2H, CH₂); 2.06 (s, 3H, CH₃); 1.75 (m, 2H, CH₂); 1.45 (s, 6H, 2CH₃).

Example 39

N-[4-{4,4-dimethyl-2,5-dioxo-3-[2-(2-{2-[(4,4,5,5,5-pentafluoropentyl)sulphinyl]ethoxy}ethoxy)ethyl]imidazolidin-1-yl}-2-(trifluoromethyl)phenyl]acetamide Compound 39 described below was synthesized according to a similar method to that described in Example 2 using the compound of Example 38 as starting reagent replacing the compound of Example 1. The expected compound is obtained in the form of a pale yellow oil with a yield of 75%.

$^1$H NMR 400 MHz (DMSO-d$_6$) δ: 9.64 (s, 1H, Ph); 7.81 (s, 1H, Ph); 7.68 (m, 1H, Ph); 7.59 (m, 1H, Ph); 3.59 (m, 10H, 5×CH$_2$); 2.98 (m, 1H, CH); 2.86 (m, 3H, CH$_2$+CH); 2.38 (m, 2H, CH$_2$); 2.06 (s, 3H, CH$_3$); 1.91 (m, 2H, CH$_2$); 1.45 (s, 6H, 2CH$_3$).

Example 40

N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N-methylacetamide NaH (to 60%) (6 mg, 0.16 mmole) is added under argon to a solution of N-[4-(4,4-dimethyl-2,5-dioxo-3-{9-[(4,4,5,5,5-pentafluoropentyl)sulphinyl]-nonyl}imidazolidin-1-yl)-2 (trifluoromethyl)phenyl]acetamide (100 mg, 0.15 mmole) (prepared according to Example 18) in anhydrous DMF (2 ml). A release of gas accompanies the change in colour of the reaction medium. Stirring is maintained for 1 hour at 23° C. before adding methyl iodide (10 µl, 0.16 mmole). After reaction for 1 hour the same quantity of sodium hydride and methyl iodide as previously are added, then the reaction mixture is again stirred for 3 hours at 23° C. The reaction medium is poured into water (25 ml) and extracted with AcOEt (2×25 ml). The organic phases are combined and washed successively with water (25 ml) and salt water (25 ml). After drying over Na$_2$SO$_4$, the organic solution is filtered and concentrated under vacuum. The evaporation residue is purified on a silica column (eluent: CH$_2$Cl$_2$/MeOH: 95/5 to 90/10). The expected compound is obtained in the form of a colourless oil with a yield of 72% (72 mg).

$^1$H NMR 400 MHz (DMSO-d$_6$) δ: 7.98 (d, 1H, Ph); 7.86 (m, 1H, Ph); 7.73 (d, 1H, Ph); 3.28 (m, 2H, NCH$_2$); 3.08 (s, 3H, CH$_3$); 2.85 (m, 4H, 2CH$_2$); 2.38 (m, 2H, CH$_2$); 1.90 (m, 2H, CH$_2$); 1.66 (s, 5H, CH$_3$—CO, CH$_2$); 1.44 (s, 6H, 2×CH$_3$); 1.30 (m, 4H, 2×CH$_2$); 1.30 (m, 8H, 4×CH$_2$).

Example 41

N-[4-(4,4-dimethyl-2,5-dioxo-3-{9-[(4,4,5,5,5-pentafluoropentyl)sulphinyl]nonyl}imidazolin-1-yl)-2-(trifluoromethyl)phenyl]methanesulphonamide 41.1) N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N-(methylsulphonyl) methanesulphonamide Sulphonyl chloride (193 µl, 10 eq.) is added dropwise at 23° C. to a solution of Example 16 (151 mg, 0.25 mmole) in anhydrous CH$_2$Cl$_2$ (5 ml). Stirring is maintained for 15 hours at 23° C. then sulphonyl chloride (0.58 ml, 30 eq.) and diisopropylethylamine (1.75 ml, 40 eq.) are added. Stirring is maintained for 3 hours at 23° C. then the reaction mixture is concentrated to dryness under vacuum. The evaporation residue is diluted with a solvent mixture of tetrahydrofuran/methanol/water 1/1/1 (3 ml) and lithium hydroxide (25 mg, 1 mmol) is added. Stirring is maintained for 15 hours at 23° C. then lithium hydroxide is added (50 mg, 2 mmol.) in a solvent mixture of tetrahydrofuran/methanol/water 2/2/2 (6 ml). After 2 hours at 23° C. the reaction medium is poured into water (25 ml) and extracted with AcOEt (2×25 ml). The organic phases are combined and washed successively with water (25 ml) and salt water (25 ml). After drying over Na$_2$SO$_4$, the organic solution is filtered and concentrated under vacuum. The evaporation residue is purified on a silica column (eluent: Heptane/AcOEt:7/3 to 5/5). After collection and concentration of the pure fractions, the expected compound is obtained in the form of a colourless oil which crystallizes slowly with a yield of 47% (81 mg).

MH+ experimental=684.1; M theoretical=683.2

41.2) N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]methanesulphonamide Compound 41 described below was synthesized according to a method similar to that described in Example 2 using the compound of Example 41.1 as starting reagent replacing the compound of Example 1. The expected compound is obtained in the form of a pale yellow oil with a yield of 71%.

$^1$H NMR 400 MHz (DMSO-d$_6$) δ: 9.54 (s, 1H, Ph); 7.84 (d, 1H, Ph); 7.72 (m, 2H, Ph); 3.28 (m, 2H, CH$_2$); 3.13 (s, 3H, CH$_3$); 2.75 (m, 4H, 2CH$_2$); 2.38 (m, 2H, CH$_2$); 1.90 (m, 2H, CH$_2$); 1.61 (m, 4H, 2CH$_2$); 1.45 (s, 6H, 2CH$_3$): 1.30 (m, 10H, 5CH$_2$).

Example 42

N-[4-(4,4-dimethyl-2,5-dioxo-3-{9-[(4,4,5,5,5-pentafluoropentyl)sulphanyl]nonyl}imidazolidin-1-yl)-2-(trifluoromethyl)phenyl]-N$^2$,N$^2$-dimethylglycinamide Compound 41 described below was synthesized according to a method similar to that described in Example 17 using dimethyl amino acetyl chloride in its hydrochloride form as starting reagent replacing acetyl chloride. The expected compound is obtained in the form of a pale yellow oil with a yield of 83%.

$^1$H NMR 400 MHz (DMSO-d$_6$) δ: 9.85 (s, 1H, Ph); 8.19 (d, 1H, Ph); 7.81 (d, 1H, Ph); 7.57 (m, 1H, Ph); 3.27 (s, 2H, CH$_2$); 3.12 (m, 2H, CH$_2$); 2.57 (m, 2H, CH$_2$); 2.46 (m, 2H, CH$_2$); 2.30 (m, 8H, 2CH$_3$, CH$_2$); 1.75 (m, 2H, CH$_2$); 1.60 (m, 2H, CH$_2$); 1.45 (s, 8H, 2CH$_3$, CH$_2$); 1.30 (m, 10H, 5CH$_2$).

Example 43a

N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N$^2$,N$^2$-dimethylglycinamide Compound 43a described below was synthesized according to a method similar to that described in Example 2 using the compound of Example 42 as starting reagent replacing the compound of Example 1. The expected compound is obtained in the form of a pale yellow oil with a yield of 65%.

$^1$H NMR 400 MHz (DMSO-d$_6$) δ: 9.85 (s, 1H, Ph); 8.19 (d, 1H, Ph); 7.81 (d, 1H, Ph); 7.70 (m, 1H, Ph); 3.19 (s, 2H, CH$_2$); 2.75 (m, 4H, 2CH$_2$): 2.30 (m, 8H, 2CH$_3$, CH$_2$); 1.90 (m, 2H, CH$_2$); 1.60 (m, 4H, 2CH$_2$); 1.45 (s, 8H, 2CH$_3$, CH$_2$); 1.30 (m, 10H, 5CH$_2$).

Example 43b

N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N$^2$,N$^2$-dimethylglycinamide hydrochloride A solution of hydrochloric acid in the 2N ether (904 µl, 2 eq.) is added dropwise at 23° C. to a solution of Example 43a (639 mg, 0.904 mmole) in anhydrous ether (35 ml). Stirring is maintained for 15 hours at 23° C. then the reaction mixture is concentrated to dryness under vacuum having been taken up twice with ether (2×20 ml) then twice with isopentane (2×20 ml). The evaporation residue is dried under vacuum at 55° C. The expected compound is obtained in the form of a beige-coloured powder with a yield of 93% (624 mg).

$^1$H NMR 400 MHz (DMSO-$d_6$) δ: 10.52 (s, 1H, Ph); 10.06 (s, 1H, Ph); 7.89 (s, 1H, Ph); 7.78 (m, 1H, Ph); 7.67 (m, 1H, Ph); 4.14 (m, 2H, $CH_2$); 2.84 (s, 6H, $2CH_3$); 2.70 (m, 4H, $2CH_2$); 2.36 (m, 2H, $CH_2$); 1.94 (m, 2H, $CH_2$); 1.60 (m, 4H, $2CH_2$); 1.45 (s, 8H, $2CH_3$, $CH_2$); 1.30 (m, 10H, $5CH_2$).

Example 44

N-[(1Z)-(9-{5,5-dimethyl-3-[4-nitro-3-(trifluoromethyl)phenyl]-2,4-dioxoimidazolidin-1-yl}nonyl)(4,4,5,5,5-pentafluoropentyl)-$\lambda^4$-sulphanylidene]-2,2,2-trifluoroacetamide 2,2,2-trifluoroacetamide (106 mg, 0.94 mmole), magnesium oxide (76 mg, 4 eq.), rhodium acetate in the dimer form (5.2 mg, 0.025 eq.) and iodobenzene diacetate (228 mg, 1.5 eq.) are added at 23° C. to a solution of Example 1 (300 mg, 0.48 mmole) in anhydrous $CH_2Cl_2$ (5 ml). Stirring is maintained for 6 hours at 23° C. then the reaction mixture is filtered under vacuum. The filtrate is poured into water (25 ml) and extracted with AcOEt (2×25 ml). The organic phases are combined and washed successively with water (25 ml) and salt water (25 ml). After drying over $Na_2SO_4$, the organic solution is filtered and concentrated under vacuum. The evaporation residue is purified on a silica column (eluent: Heptane/AcOEt:5/5 to 3/7). After collection and concentration of the pure fractions, the expected compound is obtained in the form of a colourless oil with a yield of 34% (77 mg).

$^1$H NMR 400 MHz (DMSO-$d_6$) δ: 8.32 (d, 1H, Ph); 8.20 (d, 1H, Ph); 8.06 (dd, 1H, Ph); 3.30 (m, 214, $NCH_2$); 3.10 (m, 4H, $CH_2S(=NCOCF_3)CH_2$); 2.40 (m, 2H, $CH_2$); 1.92 (m, 2H, $CH_2$); 1.65 (m, 4H, $2×CH_2$); 1.48 (s, 6H, $2×CH_3$); 1.42 (m, 2H, $CH_2$); 1.34 (m, 8H, $4×CH_2$).

Example 45

N-[(9-{5,5-dimethyl-3-[4-nitro-3-(trifluoromethyl)phenyl]-2,4-dioxoimidazolidin-1-yl}nonyl)(oxido)(4,4,5,5,5-pentafluoropentyl)-$\lambda^4$-sulphanylidene]-2,2,2-trifluoroacetamide 2,2,2-trifluoroacetamide (38 mg, 0.33 mmole), magnesium oxide (27 mg, 4 eq.), rhodium acetate in the dimer form (1.8 mg, 0.025 eq.) and iodobenzene diacetate (81 mg, 1.5 eq.) are added at 23° C. to a solution of Example 2 (109 mg, 0.17 mmole) in anhydrous $CH_2Cl_2$ (5 ml). Stirring is maintained for 6 hours at 23° C. then the reaction mixture is filtered under vacuum. The filtrate is poured into water (25 ml) and extracted with AcOEt (2×25 ml). The organic phases are combined and washed successively with water (25 ml) and salt water (25 ml). After drying over $Na_2SO_4$, the organic solution is filtered and concentrated under vacuum. The evaporation residue is purified on a silica column (eluent: Heptane/AcOEt:5/5 to 2/8). After collection and concentration of the pure fractions, the expected compound is obtained in the form of a colourless oil with a yield of 88% (114 mg).

$^1$H NMR 400 MHz (DMSO-$d_6$) δ: 8.32 (d, 1H, Ph); 8.20 (d, 1H, Ph); 8.06 (dd, 1H, Ph); 3.76 (m, 4H, $CH_2S(=O)(=NCOCF_3)CH_2$); 3.30 (m, 2H, $NCH_2$); 2.48 (m, 2H, $CH_2$); 2.02 (m, 2H, $CH_2$); 1.70 (m, 4H, $2×CH_2$); 1.46 (s, 6H, $2×CH_3$); 1.42 (m, 2H, $CH_2$); 1.34 (m, 8H, $4×CH_2$).

Example 46

5,5-dimethyl-3-[4-nitro-3-(trifluoromethyl)phenyl]-1-{9-[S-(4,4,5,5,5-pentafluoropentyl)sulphonimidoyl]nonyl}imidazolidine-2,4-dione Potassium carbonate (35 mg, 0.25 mmole) is added at 23° C. to a solution of Example 45 (38 mg, 0.05 mmole) in anhydrous MeOH (0.5 ml). Stirring is maintained for 15 hours at 23° C. then the reaction mixture is filtered under vacuum. The filtrate is poured into water (25 ml) and extracted with AcOEt (2×25 ml). The filtrate is concentrated under vacuum. The evaporation residue is purified on a silica column (eluent 2×10 ml with AcOEt/$CH_2Cl_2$: 5/5 then 10 ml with AcOEt/Heptane 7.5/2.5). After collection and concentration of the pure fractions, the expected compound is obtained in the form of a colourless oil with a yield of 67% (22 mg).

$^1$H NMR 400 MHz (DMSO-$d_6$) δ: 8.28 (d, 1H, Ph); 8.17 (d, 1H, Ph); 8.03 (dd, 1H, Ph); 3.65 (s, 1H, NH); 3.30 (m, 2H, $NCH_2$); 3.10 (m, 4H, $CH_2S(=NH)CH_2$); 2.31 (m, 2H, $CH_2$); 1.92 (m, 2H, $CH_2$); 1.65 (m, 4H, $2×CH_2$); 1.43 (s, 6H, $2×CH_3$); 1.42 (m, 2H, $CH_2$); 1.34 (m, 8H, $4×CH_2$).

Pharmacological Study of the Compounds According to the Invention

Measurements of Anti-Proliferative Activities:

1. Anti-Proliferative Activity on LNCaP in Complete Medium

The anti-proliferative activity of the compounds of the present invention is determined on LNCaP in complete medium by applying the following experimental procedure:

The LNCaP cell type (ATCC, 1740) originating from a prostate carcinoma expressing the androgen receptor, this line is hormone-dependent.

Maintenance of the LNCaP line is carried out in complete culture medium: RPMI, 10% of foetal calf serum, 2 mM glutamine, 100 U/ml penicillin, 0.1 mg/ml of streptomycin and 0.01M HEPES, 1 mM sodium pyruvate, 40% of D-glucose.

Seeding the plates:

The LNCaP line is seeded at 20,000 cells/well in 90 μl of complete medium in 96-well plates coated with poly-D-lysine (Biocoat, Costar).

Treatment of the cells: 24 h after the seeding, the cells are treated with 10 μl/well of compound diluted in the culture medium. Experiments of the effect of doses of the compound are carried out on a scale of 1 nM to 100 M. The concentrations used are the following: 1 nM/10/30/100/300/1000/3000/10,000/100,000 nM. Testosterone (SIGMA T1500) is used as a reference and tested at the same concentrations. The cells are incubated for 144 h at 37° C., 5% $CO_2$.

Reading: On D6, 10 μL of the "WST-1 cell proliferation" reagent (Roche ref 1644807) is added to each well. After incubation for 2 hours at 37° C., 5% $CO_2$, the absorbance at 450 nm is measured by spectrophotometry (Envision, Perkin Elmer).

Results: The experiments are carried out in duplicate and the best compounds are tested twice. A concentration value inhibiting the proliferation cell by 50% ($IC_{50}$) is calculated.

The compounds of the following examples have an $IC_{50}$ of less than 2000 nM on the LNCaP cells in culture: 1, 2, 3, 4, 5, 7, 9, 11, 12, 13, 15, 17, 18, 20, 22, 24, 28, 30, 31, 32, 34, 35, 36, 37, 38, 40, 41, 42, 43, 44, 45 and 46.

Among those, the compounds of the following examples have an $IC_{50}$ of less than 1000 nM on the LNCaP cells in culture: 2, 3, 9, 12, 13, 15, 17, 18, 20, 22, 24, 32, 34, 35, 36, 38, 41, 43, 44, 45 and 46.

The compounds of the following examples have an $IC_{50}$ of less than 500 nM on the LNCaP cells in culture: 2, 9, 12, 13, 18, 35, 36, 38, 43, 44 and 45.

2. Antiproliferative Activity on LNCaP in Medium without Steroids:

The anti-proliferative activity of the compounds of the present invention is determined on LNCaP in medium without steroids.

The maintenance of the LNCaP line is carried out under the usual conditions in RPMI, 10% of foetal calf serum, 2 mM of glutamine, 100 U/ml of penicillin, 0.1 mg/ml of streptomycin and 0.01M HEPES, 1 mM sodium pyruvate, 40% of D-glucose.

For the study under conditions without steroids, 24 hours before the seeding the culture medium of the cells is eliminated. The cells are washed with PBS, then incubated in the presence of RPMI medium without phenol red, 10% of foetal calf serum without steroids (treatment with carbon), 2 mM of glutamine, 100 U/ml of penicillin, 0.1 mg/ml of streptomycin and 0.01M HEPES, 1 mM of sodium pyruvate, 40% of D-glucose.

Seeding the plates:
The LNCaP line is seeded at 20,000 cells/well in 90 µl of RPMI medium with 10% foetal calf serum without steroids in 96-well plates coated with poly-D-lysine (Biocoat, Costar).

Treatment of the cells: 24 h after seeding, the cells are treated with 10 µl/well of compound diluted in the culture medium. Experiments showing the dose-effect of the compound are carried out on a scale of 1 nM to 100 µM. The concentrations used are the following: 1 nM/10/30/100/300/1000/3000/10,000/100,000 nM. Testosterone (SIGMA T1500) is used as a reference and tested at the same concentrations. The cells are incubated for 144 h at 37° C., 5% $CO_2$.

Reading: On D6, 10 µL of cell proliferation reagent WST-1 (Roche ref 1644807) is added to each well. After incubation for 2 to 4 hours at 37° C., 5% $CO_2$, the absorbance at 450 nm is measured by spectrophotometry (Envision, Perkin Elmer).

Results: The experiments are carried out in duplicate and the best compounds are tested twice. A concentration value inhibiting proliferation cell by 50% ($IC_{50}$) is calculated.

The products of Examples 1 to 46 do not exhibit an agonist effect on LNCaP in medium without steroids.

FIG. 1 shows the effect of the compounds of Examples 18 and 43a on the cell proliferation of LNCaP cultured in medium without steroids.

Compounds 18 and 43a surprisingly show an anti-proliferative activity on the LNCaP cells without an agonist effect. Quite the reverse, nilutamide has a biphasic profile with an agonist activity at low concentration followed by an inhibitory activity at high concentration.

3. Antiproliferative Activity on DU-145 in Complete Medium:

The anti-proliferative activity of the compounds of the present invention is determined on DU-145 in complete medium.

Maintenance of the DU-145 line is carried out in DMEM, 10% of foetal calf serum, 2 mM of glutamine, 100 U/ml of penicillin, 0.1 mg/ml of streptomycin.

Seeding the plates:
The DU145 line is seeded at 400 or 800 cells/well in 90 µl of DMEM complete medium in 96-well plates (TPP).

Treatment of the cells: 24 h after the seeding, the cells are treated with 10 µl/well of compound diluted in the culture medium. Experiments showing the dose-effect of the compound are carried out on a scale of 1 nM to 100 µM. The concentrations used are the following: 1 nM/10/30/100/300/1000/3000/10,000/100,000 nM. The cells are incubated for 144 h at 37° C., 5% $CO_2$.

Reading: On D6, 10 µL, of cell proliferation reagent WST-1 (Roche ref 1644807) is added to each well. After incubation for 2 to 4 hours at 37° C., 5% $CO_2$, the absorbance at 450 nm is measured by spectrophotometry (Envision, Perkin Elmer).

Results: The experiments are carried out in duplicate and the best compounds are tested twice. A concentration value inhibiting the cell proliferation by 50% ($IC_{50}$) is calculated.

The compounds of the following examples have an $IC_{50}$ greater than 10,000 nM on the DU145 cells in culture: 1, 2, 3, 4, 5, 7, 8, 9, 11, 14, 15, 16, 17, 18, 20, 22, 24, 26, 28, 30, 31, 32, 34, 35, 36, 37, 38, 39, 40, 41, 42, 43, 44 and 45.

4. Measurement of the Disappearance of the Androgen Receptor

It will be shown that the compounds reduce the level of protein expression of the androgen receptor.

The cells of the LNCaP line are seeded at a rate of 2.5 millions of cells per 10 cm Petri dish in RPMI, 10% of foetal calf serum, 2 mM of glutamine, 100 U/ml of penicillin, 0.1 mg/ml of streptomycin and 0.01M HEPES, 1 mM of sodium pyruvate, 40% of D-glucose. 4 days later, the cells are treated with the compound to be tested. 72 hours after the treatment the cells are lyzed in lysis buffer (50 mM Tris pH 7.4, 150 mM NaCl, 1 mM EDTA, 20 mM NaF, 100 mM $Na_2VO_3$, 0.5% of NP40, 1% of Triton X-100, 1 mM EGTA, Pefabloc, protease inhibitor cocktail 11836170001 RocheDiagnostics, Phosphatase inhibitor cocktail set II Calbiochem). The cells are then scrapped and the lysate transferred into QIAshredder tubes (cat No. 79656 Qiagen) for centrifugation at 13,000 rpm for 15 min at 4° C. The supernatant is transferred into QIAshredder tubes for a second centrifugation at 13,000 rpm for 5 min in order to completely eliminate the DNA filaments. After freezing at −80° C., the protein concentration is determined (Bio-Rad DC protein assay kit) and adjusted to between 10 and 20 µl per well. The loading buffer (sample loading buffer 3×ref 7722 Cell signaling technology) with added 1% beta-mercaptoethanol and 50 mM DTT, is added to the samples which are then heated for 10 min at 90° C. The samples are deposited under a volume of 20 µl on NuPAGE 4-12% Bis-Tris gels (cat No. NP0322BOX, Invitrogen). The migration takes place in MOPS buffer (Invitrogen) and is carried out for 1 hour at 180V. The proteins are transferred onto a nitrocellulose membrane (Hybond ECL RPN78D, GE Healthcare) under semi-dry conditions, in the presence of transfer buffer (NP0006-1, Invitrogen) over 45 min at 15V. The membrane is then blocked for 1 hour in blocking buffer (Non-fat dry milk, cat 170-6404, Biorad) at 5% in TBS 0.1% Tween 20. Then it is incubated at 4° C. overnight in the presence of primary antibody directed against the androgen receptor (AR441, sc-7305, Santa Cruz) diluted to 1/2000th in blocking buffer as well as in the presence of primary antibody directed against GAPDH (Cat.MAB374, Millipore) diluted to 1/20,000[th] in blocking buffer (monitoring of protein load). The membrane is then washed 3 times in washing buffer (TBS, 0.1% Tween 20). The membrane is then incubated in

The invention claimed is:

1. A compound formula (I)

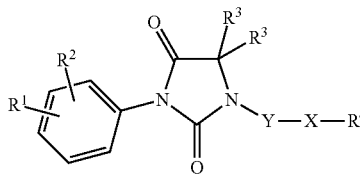

in racemic or enantiomeric form or any combination thereof, wherein $R^1$ and $R^2$ represent independently a halogen atom, or an alkyl, haloalkyl, alkoxy, cyano, nitro, amino, alkylamino, dialkylamino, —$NR^8$—CO—$R^5$, —$NR^8$—$SO_2$—$R^5$, —$NR^8$—CO—$(CH_2)_n$—$NR^6$, $R^7$, —$NR^8$—$SO_2$—$(CH_2)_n$—$NR^6R^7$, or —CO—$NH_2$ radical;

n represents an integer chosen from 0, 1, 2, 3, 4, 5, or 6;

$R^5$ represents an alkyl, aryl, or heteroaryl radical;

$R^6$ and $R^7$ represent independently a hydrogen atom, an alkyl, or an alkyloxycarbonyl radical;

$R^8$ represents a hydrogen atom or an alkyl radical;

$R^3$ represents an alkyl radical or a hydrogen atom; or the two $R^3$ radicals form together with the carbon atom to which they are attached a cycloalkyl radical comprising 3 to 6 members;

$R^4$ represents a haloalkyl radical with 2 to 10 carbon atoms;

Y represents a linear or branched alkylene chain with 2 to 14 carbon atoms, wherein the chain is saturated or unsaturated, and optionally comprising one or more additional —O—members;

X represents —S—, —SO—, —$SO_2$—, —S=N($R^9$)— or —S(O)=N($R^9$)—;

$R^9$ represents a hydrogen atom or a haloalkylcarbonyl radical, or a pharmaceutically acceptable salt thereof.

2. The compound according to claim 1, wherein $R^1$ represents a halogen atom, or an alkyl, alkoxy, cyano, nitro, amino, alkylamino, dialkylamino, —$NR^8$—CO—$R^5$, —$NR^8$—$SO_2$—$R^5$, —$NR^8$—CO—$(CH_2)_n$—$NR^6R^7$, —$NR^8$—$SO_2$—$(CH_2)_n$—$NR^6R^7$, or —CO—$NH_2$ radical; $R^2$ represents a halogen atom, an alkyl, or haloalkyl radical.

3. The compound according to claim 1, wherein $R^5$ represents an alkyl radical.

4. The compound according to claim 1, wherein $R^3$ represents an alkyl radical.

5. The compound according to claim 1, wherein $R^4$ represents a haloalkyl radical comprising 4 to 6 carbon atoms and 3 to 9 fluorine atoms; and Y represents an alkylene chain with 5 to 10 carbon atoms.

6. The compound according to claim 1, wherein $R^1$ is in para position.

7. The compound according to one of claim 1, wherein $R^2$ is in meta position.

8. The compound according to one of claim 1, wherein:
$R^1$ represents a cyano, nitro, amino, —$NR^8$—CO—$R^5$, —$NR^8$—$SO_2$—$R^5$, —$NR^8$—CO—$(CH_2)_n$—$NR^6R^7$, —$NR^8$—$SO_2$—$(CH_2)_n$—$NR^6R^7$, or —CO—$NH_2$ radical;

$R^2$ represents an alkyl or haloalkyl radical;

$R^5$ represents an alkyl radical;

$R^6$ and $R^7$ represent independently a hydrogen atom, an alkyl, or alkyloxycarbonyl radical;

$R^3$ represents an alkyl radical or the two $R^3$ radicals form together with the carbon atom to which they are attached a cycloalkyl radical comprising 3 to 6 members;

$R^4$ represents a haloalkyl radical comprising 4 to 6 carbon atoms and 3 to 9 fluorine atoms;

n is equal to 0 or 1;

$R^9$ represents a hydrogen atom or —$COCF_3$;

or a pharmaceutically acceptable salt thereof.

9. The compound according to claim 1, wherein $R^1$ represents a cyano, nitro, —$NR^8$—CO—$R^5$, —$NR^8$—$SO_2$—$R^5$, —$NR^8$—CO—$(CH_2)_n NR^6R^7$, —$NR^8$—$SO_2$—$(CH_2)_n$—$NR^6R^7$, or —CO—$NH_2$ radical; n is equal to 0 or 1; $R^5$ represents an alkyl radical, $R^6$ and $R^7$ represent independently a hydrogen atom or an alkyl radical, and $R^2$ represents an alkyl or haloalkyl radical.

10. The compound according to claim 1, wherein $R^1$ represents a nitro or —$NR^8$—CO—$R^5$ radical and wherein $R^5$ represents an alkyl radical.

11. The compound according to claim 1, wherein the alkyl radical represents a methyl group and/or the haloalkyl radical represents a trifluoromethyl group, or a radical of molecular formula $C_5H_6F_5$, $C_5H_4F_7$, $C_6H_8F_5$, $C_6H_6F_7$ or $C_6H_4F_9$.

12. The compound according to claim 1, wherein Y represents an alkylene chain with 9 to 10 carbon atoms.

13. The compound according to claim 1, wherein the compound is selected from 5,5-dimethyl-3-[4-nitro-3-(trifluoromethyl)phenyl]-1-{9-[(4,4,5,5,5-pentafluoropentyl)sulphinyl]nonyl}imidazolidine-2,4-dione;

5,5-dimethyl-3-[4-nitro-3-(trifluoromethyl)phenyl]-1-{10-[(4,4,5,5,5-pentafluoropentyl)sulphinyl]decyl}imidazolidine-2,4-dione;

5,5-dimethyl-3-[4-nitro-3-(trifluoromethyl)phenyl]-1-{9-[(4,4,4-trifluorobutyl)thio]nonyl}imidazolidine-2,4-dione;

5,5-dimethyl-3-[4-nitro-3-(trifluoromethyl)phenyl]-1-{9-[(4,4,4-trifluorobutyl)sulphinyl]nonyl}imidazolidine-2,4-dione;

N-[4-(4,4-dimethyl-2,5-dioxo-3-{9-[(4,4,5,5,5-pentafluoropentyl)sulphinyl]-nonyl}imidazolidin-1-yl)-2-(trifluoromethyl)phenyl]acetamide;

N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N2,N2-dimethylglycinamide; or N-[4-(4,4-dimethyl-2,5-dioxo-3-{9-[(4,4,5,5,5-pentafluoropentyl)sulphinyl]nonyl}imidazolidin-1-yl)-2-(trifluoromethyl)phenyl]-N2,N2-dimethylglycinamide hydrochloride;

or a pharmaceutically acceptable salt thereof.

14. The compound according to claim 1, wherein the compound is N-[4-(4,4-dimethyl-2,5-dioxo-3-{9-[(4,4,5,5,5-pentafluoropentyl)sulphinyl]-nonyl}imidazolidin-1-yl)-2-(trifluoromethyl)phenyl]acetamide or a pharmaceutically acceptable salt thereof.

15. A method of preparing the compound according to claim 1, comprising
condensing hydantoin derivatives of general formula (II)

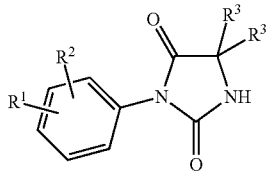

(II)

in the presence of a strong base, at a temperature range between 25° C. and 60° C., in an anhydrous polar solvent, on mesylate derivatives of general formula (III),

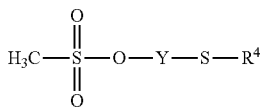

(III)

or treating thiobenzoyl derivatives of general formula (V),

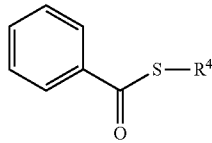

(V)

with an alcoholate in a polar protic solvent, followed by adding a halogenated derivative of general formula (IV) to the thiobenzoyl derivative,

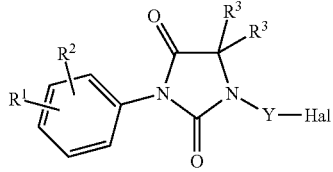

(IV)

in solution in a polar solvent solution.

16. A method of preparing a compound of formula I.2

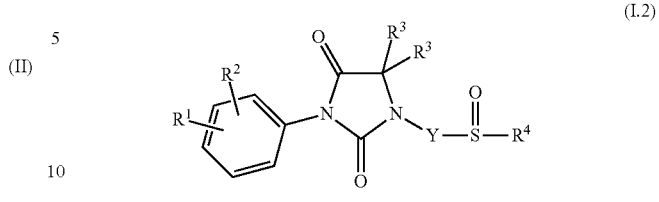

(I.2)

comprising
oxidizing the compounds of formula of claim 1 to obtain a sulphoxide of formula (I.2).

17. A method of preparing a compound of formula (I.3)

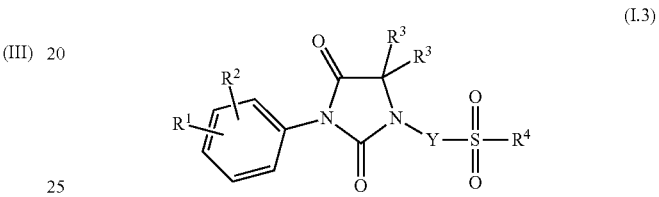

(I.3)

comprising oxidizing the compound of formula (I.2) of claim
to obtain a sulphone of formula (I.3).

18. An intermediate compound selected from:
1-(5-iodopentyl)-5,5-dimethyl-3-[4-nitro-3-(trifluoromethyl)phenyl]imidazolidine-2,4-dione;
1-(8-iodooctyl)-5,5-dimethyl-3-[4-nitro-3-(trifluoromethyl)phenyl]imidazolidine-2,4-dione;
1-(9-bromononyl)-5,5-dimethyl-3-[4-nitro-3-(trifluoromethyl)phenyl]imidazolidine-2,4-dione;
4-[3-(9-bromononyl)-4,4-dimethyl-2,5-dioxoimidazolidin-1-yl]-2-(trifluoromethyl)benzonitrile;
5,5-dimethyl-3-(3-methyl-4-nitrophenyl)imidazolidine-2,4-dione; or
1-(9-bromononyl)-5,5-dimethyl-3-(3-methyl-4-nitrophenyl)imidazolidine-2,4-dione.

19. A pharmaceutical composition comprising, as an active ingredient, the compound according to claim 1, and at least one pharmaceutically acceptable excipient.

20. A method of treating breast or prostate cancer comprising administering to a subject in need thereof a therapeutically effective amount of a compound according to claim 1.

21. The method according to claim 20, wherein the cancer is prostate cancer.

* * * * *

UNITED STATES PATENT AND TRADEMARK OFFICE
CERTIFICATE OF CORRECTION

PATENT NO. : 8,710,091 B2  
APPLICATION NO. : 13/264971  
DATED : April 29, 2014  
INVENTOR(S) : Prevost et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 35 days.

Signed and Sealed this

Twenty-ninth Day of September, 2015

Michelle K. Lee
*Director of the United States Patent and Trademark Office*